US009145551B2

(12) United States Patent
Fox et al.

(10) Patent No.: US 9,145,551 B2
(45) Date of Patent: Sep. 29, 2015

(54) MULTIFUNCTIONAL CELLULASE AND HEMICELLULASE

(71) Applicant: Wisconsin Alumni Research Foundation, Madison, WI (US)

(72) Inventors: Brian G. Fox, Madison, WI (US); Taichi Takasuka, Madison, WI (US); Christopher M. Bianchetti, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/030,290

(22) Filed: Sep. 18, 2013

(65) Prior Publication Data
US 2014/0079683 A1 Mar. 20, 2014

Related U.S. Application Data

(60) Provisional application No. 61/703,063, filed on Sep. 19, 2012.

(51) Int. Cl.
C12N 9/42 (2006.01)
C07K 14/33 (2006.01)

(52) U.S. Cl.
CPC .............. *C12N 9/2437* (2013.01); *C07K 14/33* (2013.01)

(58) Field of Classification Search
None
See application file for complete search history.

(56) References Cited

U.S. PATENT DOCUMENTS

| | | | |
|---|---|---|---|
| 7,601,358 | B2 | 10/2009 | Fox |
| 8,043,839 | B2 | 10/2011 | Weiner et al. |
| 8,088,601 | B2 | 1/2012 | Fox |
| 8,268,581 | B2 | 9/2012 | Fox |
| 2006/0105442 | A1 | 5/2006 | Wu et al. |
| 2008/0182249 | A1 | 7/2008 | Fox |
| 2008/0286749 | A1 | 11/2008 | Fox |
| 2010/0304405 | A1 | 12/2010 | Fox et al. |

FOREIGN PATENT DOCUMENTS

| | | |
|---|---|---|
| WO | 02/079403 A2 | 10/2002 |
| WO | 2004/096999 A2 | 11/2004 |
| WO | 2007/139608 A1 | 12/2007 |
| WO | 2008/028147 | 3/2008 |
| WO | 2008/127997 | 10/2008 |
| WO | 2009/064954 | 5/2009 |
| WO | 2010/141604 | 12/2010 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Hughes et al., "High-throughput screening of cellulose F mutants from multiplexed plasmid sets using an automated plate assay on a functional proteomic robotic workcell," Proteome Science, Biomed Central, London, Great Britain, DOI:10.1186/1477-5956-4-10; vol. 4, No. 1, May 2, 2006, pp. 1-14.
International Searching Authority, "PCT International Search Report," International application No. PCT/US2010/037094, European Patent Office, Jan. 13, 2011, pp. 1-8.
Haimovitz et al., "Cohesin-dockerin Microarray: Diverse specificities between two complementary families of interacting protein modules," 2008 Proteomics 8: 968-979.
Fierobe et al., "Action of Designer Cellulosomes on Homogeneous Versus Complex Substrates," 2005 J. Biol. Chem. 280: 16325-16334.
Heyman et al., "Multiple display of catalytic modules on a protein scaffold: Nano Fabrication of enzyme particles," 2007 Journal of Biotechnology 131: 433-439.
Arai et al., "Characterization of a Cellulase Containing a Family 30 Carbohydrate-Binding Module (CBM) Derived From *Clostridium thermocellum* CEIJ: Importance of the CBM to Cellulose Hydrolysis," Journal of Bacteriology 2003, 185(2):504-512.
Zverlov et al., "A major new component in the cellulosome of *Clostridium thermocellum* is a processive endo-B-1, 4-glucanase producing cellotetrase," FEMS Microbiology Letters 249, 353-358, 2005.
Abdeev M., et al., 2001. "Exploring the properties of thermostable *Clostridium thermocellum* cellulase CelE for the purpose of its expression in plants," Biochemistry (Moscow) 66, 808-813.
Chundawat et al., "Restructuring the Crystalline Cellulose Hydrogen Bond Network Enhances Its Depolymerization Rate," Journal of the American Chemical Society, 2011, 133, 11163-11174.
Blommel et al., "Enhanced bacterial protein expression during autoinduction obtained by alteration of lac repressor dosage and medium composition," Biotechnol Prog. 2007, 23, 585-598.
Jeon et al., "High-throughput purification and quality assurance of *Arabidopsis thaliana* proteins for eukaryotic structural genomics," Journal of Structural and Functional Genomics 2005, 6, 143-147.
Blommel et al. "A combined approach to improving large-scale production of tobacco etch virus protease," Protein Expr. Purif. 2007, 55, 53-68.
Miller, "Use of Dinitrosalicylic Acid Reagent for Determination of Reducing Sugar," Analytical Chemistry, 1959, 31(3):426-428.
Reindl et al., "Colloid-based multiplexed screening for plant biomass-degrading glycoside hydrolase activities in microbial communities," Energy Environ. Sci. 2011, 4, 2884-2893.
Reindl et al., "Nanostructure-initiator mass spectrometry (NIMS) for the analysis of enzyme activities," Current Protocols in Chemical Biology 2012, Jun. 1, 123-142.
Adams et al., "Cellulose-degrading bacteria associated with the invasive woodwasp Sirex noctilio," The ISME Journal 5, 1323-1331 (2011).
Takasuka et al. "Aerobic deconstruction of cellulosic biomass by an insect-associated Streptomyces," Scientific Reports, 3, 1-10 (2013).
Adams et al, "Cellulolytic associations of Sirex noctilio within the context of a multipartite symbiosis," Entomological Society of America Meeting (Nov. 16, 2008).
Adams et al, "Cellulose-degrading microbial symbionts of the woodwasp, Sirex noctilio," The GLBRC 2008 Retreat Poster Session Abstracts (Oct. 15-18, 2008).

* cited by examiner

*Primary Examiner* — Christian Fronda
(74) *Attorney, Agent, or Firm* — Quarles & Brady LLP

(57) ABSTRACT

A multifunctional polypeptide capable of hydrolyzing cellulosic materials, xylan, and mannan is disclosed. The polypeptide includes the catalytic core (cc) of *Clostridium thermocellum* Cthe_0797 (CelE), the cellulose-specific carbohydrate-binding module CBM3 of the cellulosome anchoring protein cohesion region (CipA) of *Clostridium thermocellum* (CBM3a), and a linker region interposed between the catalytic core and the cellulose-specific carbohydrate binding module. Methods of using the multifunctional polypeptide are also disclosed.

20 Claims, 22 Drawing Sheets

```
CelE_nts (2).txt
>CelE_native_nucleotide_sequence
atgcgtgatatttcagcaatagatttggttaaagaaataaaaatcggatggaatttgggaaatactttggatgctcctacagag
actgcctggggaaatccaaggacaaccaaggcaatgatagaaaaggtaagggaaatgggctttaatgccgtcagagtgcctgtt
acctgggatacgcacatcggacctgctccggactataaaattgacgaagcatggctgaacagagttgaggaagtggtaaactat
gttcttgactgcggtatgtacgcgatcataaatcttcaccatgacaatacatggattatacctacatatgccaatgagcaaagg
agtaaagaaaaacttgtaaaagtttgggaacaaatagcaacccgttttaaagattatgacgaccatttgttgtttgagacaatg
aacgaaccgagagaagtaggttcacctatggaatggatgggcggaacgtatgaaaaccgagatgtgataaacagatttaatttg
gcggttgttaataccatcagagcaagcggcggaaataacgataaaagattcatactggttccgaccaatgcggcaaccggcctg
gatgttgcattaaacgaccttgtcattccgaacaatgacagcagagtcatagtatccatacatgcttattcaccgtatttcttt
gctatggatgtcaacggaacttcatattggggaagtgactatgacaaggcttctcttacaagtgaacttgatgctatttacaac
agatttgtgaaaaacggaagggctgtaattatcggagaattcggaaccattgacaagaacaacctgtcttcaagggtggctcat
gccgagcactatgcaagagaagcagtttcaagaggaattgctgttttctggtgggataacggctattacaatccgggtgatgca
gagacttatgcattgctgaacagaaaaactctctcatggtattatcctgaaattgtccaggctcttatgagaggtgccggcgtt
gaacctttagtttcaccgactcctacacctacattaatgccgaccccctcgcccacggtgacagcaaatattttgtacggtgac
gtaaacggggacggaaaaataaattctacagactgtacaatgctaaagagatatatttgcgtggcatagaagaattcccaagt
cctagcggaattatagccgctgacgtaaatgcggatctgaaaatcaattccaccgacttggtattgatgaaaaaatatctactg
cgctcaatagacaaatttcctgcggaggattctcaaacacctgatgaagacaatccgggcatttgtataacggaagattcgat
ttttcagatccgaacggtccgaaatgcgcctggtccggcagcaatgttgagctgaattttacggcacggaagcaagtgtgact
atcaaatccggcggtgagaactggttccaggctattgtagacggcaatcctcttcctccttttcggttaacgctactacctct
accgtaaagcttgtaagcggtcttgcagaaggagctcatcatcttgtattgtggaagaggacagaggcatccttgggagaagtt
cagttccttgggtttgattttggttcaggaaagcttcttgccgcaccgaagcctttggaaagaaagattgagtttatcggagac
tccatcacatgtcatacggaaatgaaggaacaagcaaggagcagtcttttcaccgaaaaatgaaaacagctatatgtcttat
gcggcaattacagcccgtaatttgaatgcaagtgcaaatatgattgcgtggtccggaatcggacttaccatgaactacggcgga
gccccggacctcttataatggaccgttatccttataccttcctttacagcggagtcagatgggattttagcaaatatgtgcct
caggttgttgtaatcaatcttggtaccaatgatttttctacatcatttgcagataaaacaaagtttgtaacggcatataaaaac
cttataagtgaagttcgcaggaactatccggatgcccatatattctgctgtgtcggtccgatgctttggggaacgggcctggat
ttgtgccgcagttatgttacggaagttgtaaatgattgtaacagaagcgggatttaaaggtgtattttgttgagtttccgcag
caggacggaagcaccggatacggagaagactggcatccaagtattgccacccaccagctgatggctgagcggcttactgcggaa
ataaaaaacaagcttggatgggtttaa
```

Figure 2A (SEQ ID NO:1)

```
                              CelE_AA.txt
>CelE_native_protein_sequence
MRDISAIDLVKEIKIGWNLGNTLDAPTETAWGNPRTTKAMIEKVREMGFNAVRVPVTWDTHIGPAPDYKIDEAWLNRVEEVVNY
VLDCGMYAIINLHHDNTWIIPTYANEQRSKEKLVKVWEQIATRFKDYDDHLLFETMNEPREVGSPMEWMGGTYENRDVINRFNL
AVVNTIRASGGNNDKRFILVPTNAATGLDVALNDLVIPNNDSRVIVSIHAYSPYFFAMDVNGTSYWGSDYDKASLTSELDAIYN
RFVKNGRAVIIGEFGTIDKNNLSSRVAHAEHYAREAVSRGIAVFWWDNGYYNPGDAETYALLNRKTLSWYYPEIVQALMRGAGV
EPLVSPTPTPTLMPTPSPTVTANILYGDVNGDGKINSTDCTMLKRYILRGIEEFPSPSGIIAADVNADLKINSTDLVLMKKYLL
RSIDKFPAEDSQTPDEDNPGILYNGRFDFSDPNGPKCAWSGSNVELNFYGTEASVTIKSGGENWFQAIVDGNPLPPFSVNATTS
TVKLVSGLAEGAHRLVLWKRTEASLGEVQFLGFDFGSGKLLAAPKPLERKIEFIGDSITCAYGNEGTSKEQSFTPKNENSYMSY
AAITARNLNASANMIAWSGIGLTMNYGGAPGPLIMDRYPYTLPYSGVRWDFSKYVPQVVVINLGTNDFSTSFADKTKFVTAYKN
LISEVRRNYPDAHIFCCVGPMLWGTGLDLCRSYVTEVVNDCNRSGDLKVYFVEFPQQDGSTGYGEDWHPSIATHQLMAERLTAE
IKNKLGWV
```

Figure 2B (SEQ ID NO:2)

CelE_nts (2).txt
>CelEcc_nucleotide_sequence
ggcatgcgtgatatttcagcaatagatttggttaaagaaataaaaatcggatggaatttgggaaatactttggatgctcctaca
gagactgcctggggaaatccaaggacaaccaaggcaatgatagaaaaggtaagggaaatgggctttaatgccgtcagagtgcct
gttacctgggatacgcacatcggacctgctccggactataaaattgacgaagcatggctgaacagagttgaggaagtggtaaac
tatgttcttgactgcggtatgtacgcgatcataaatgttcaccatgacaatacatggattatacctacatatgccaatgagcaa
aggagtaaagaaaaacttgtaaaagtttgggaacaaatagcaacccgttttaaagattatgacgaccatttgttgtttgagaca
atgaacgaaccgagagaagtaggttcacctatggaatggatgggcggaacgtatgaaaaccgagatgtgataaacagatttaat
ttggcggttgttaataccatcagagcaagcggcggaaataacgataaaagattcatactggttccgaccaatgcggcaaccggc
ctggatgttgcattaaacgaccttgtcattccgaacaatgacagcagagtcatagtatccatacatgcttattcaccgtatttc
tttgctatggatgtcaacggaacttcatattggggaagtgactatgacaaggcttctcttacaagtgaacttgatgctatttac
aacagatttgtgaaaaacggaagggctgtaattatcggagaattcggaaccattgacaagaacaacctgtcttcaagggtggct
catgccgagcactatgcaagagaagcagtttcaagaggaattgctgttttctggtgggataacggctattacaatccgggtgat
gcagagacttatgcattgctgaacagaaaaactctctcatggtattatcctgaaattgtccaggctcttatgagaggtgccggc
gtttaa Figure 3A (SEQ ID NO:3)

```
CelE_AA.txt
>CelEcc_protein_sequence
GMRDISAIDLVKEIKIGWNLGNTLDAPTETAWGNPRTTKAMIEKVREMGFNAVRVPVTWDTHIGPAPDYKIDEAWLNRVEEVVN
YVLDCGMYAIINVHHDNTWIIPTYANEQRSKEKLVKVWEQIATRFKDYDDHLLFETMNEPREVGSPMEWMGGTYENRDVINRFN
LAVVNTIRASGGNNDKRFILVPTNAATGLDVALNDLVIPNNDSRVIVSIHAYSPYFFAMDVNGTSYWGSDYDKASLTSELDAIY
NRFVKNGRAVIIGEFGTIDKNNLSSRVAHAEHYAREAVSRGIAVFWWDNGYYNPGDAETYALLNRKTLSWYYPEIVQALMRGAG
V
```

Figure 3B (SEQ ID NO:4)

```
CelE_nts (2).txt
>CelEcc_CBM3a_nucleotide_sequence
atgggaacaaagcttttggatgcaagcggaaacgagcttgtaatgagggggcatgcgtgatatttcagcaatagatttggttaaa
gaaataaaaatcggatggaatttgggaaatactttggatgctcctacagagactgcctgggaaatccaaggacaaccaaggca
atgatagaaaaggtaagggaaatgggctttaatgccgtcagagtgcctgttacctgggatacgcacatcggacctgctccggac
tataaaattgacgaagcatggctgaacagagttgaggaagtggtaaactatgttcttgactgcggtatgtacgcgatcataaat
cttcaccatgacaatacatggattatacctacatatgccaatgagcaaaggagtaaagaaaaacttgtaaagtttgggaacaa
atagcaacccgttttaaagattatgacgaccatttgttgtttgagacaatgaacgaaccgagagaagtaggttcacctatggaa
tggatgggcggaacgtatgaaaaccgagatgtgataaacagatttaatttggcggttgttaataccatcagagcaagcggcgga
aataacgataaaagattcatactggttccgaccaatgcggcaaccggcctggatgttgcattaaacgaccttgtcattccgaac
aatgacagcagagtcatagtatccatacatgcttattcaccgtatttctttgctatggatgtcaacggaacttcatattggga
agtgactatgacaaggcttctcttacaagtgaacttgatgctatttacaacagatttgtgaaaaacggaagggctgtaattatc
ggagaattcggaaccattgacaagaacaaacctgtcttcaaggggtggctcatgccgagcactatgcaagagaagcagtttcaaga
ggaattgctgttttctggtgggataacggctattacaatccgggtgatgcagagacttatgcattgctgaacagaaaaactctc
tcatggtattatcctgaaattgtccaggctcttatgagaggtgccggcgttgaaagtttaaacgcgactcccactaaaggtgcc
actcctaccaatacggcgactccgactaagtcggcaacggcaacgcccactcgccccagcgtaccgaccaatactccgactaat
accccggcgaacaccccagtaagcggtaacctgaaggttgaattttataactccaacccaagcgacacaacgaatagcatcaat
ccgcagttcaaagtcacgaacactggcagttcagctatcgatctgtcgaaactgaccttcgttactactatacggttgatggc
caaaaagatcagaccttttggtgcgaccatgcagcaatcatcggtagcaatggttcttataacggcattacttctaatgtaaaa
ggcacctttgtgaagatgtcaagtagcaccaacaatgctgatacctacctggaaattagcttcacgggtggcacacttgaacca
ggagcccacgtccagatccagggcgtttgcgaaaaacgattggagcaactatacgcaatcaaacgattatagtttcaaaagc
gcgtctcaattcgtagaatgggatcaggtgaccgcatatttgaacggagtgctggtttggggggaaagaaccaggatag
```

Figure 4A (SEQ ID NO:5)

```
                                    CelE_AA.txt
>CelEcc_CBM3_protein_sequence
MGTKLLDASGNELVMRGMRDISAIDLVKEIKIGWNLGNTLDAPTETAWGNPRTTKAMIEKVREMGFNAVRVPVTWDTHIGPAPD
YKIDEAWLNRVEEVVNYVLDCGMYAIINLHHDNTWIIPTYANEQRSKEKLVKVWEQIATRFKDYDDHLLFETMNEPREVGSPME
WMGGTYENRDVINRFNLAVVNTIRASGGNNDKRFILVPTNAATGLDVALNDLVIPNNDSRVIVSIHAYSPYFFAMDVNGTSYWG
SDYDKASLTSELDAIYNRFVKNGRAVIIGEFGTIDKNNLSSRVAHAEHYAREAVSRGIAVFWWDNGYYNPGDAETYALLNRKTL
SWYYPEIVQALMRGAGVESLNATPTKGATPTNTATPTKSATATPTRPSVPTNTPTNTPANTPVSGNLKVEFYNSNPSDTTNSIN
PQFKVTNTGSSAIDLSKLTLRYYYTVDGQKDQTFWCDHAAIIGSNGSYNGITSNVKGTFVKMSSSTNNADTYLEISFTGGTLEP
GAHVQIQGRFAKNDWSNYTQSNDYSFKSASQFVEWDQVTAYLNGVLWGKEPG
```

Figure 4B (SEQ ID NO:6)

B
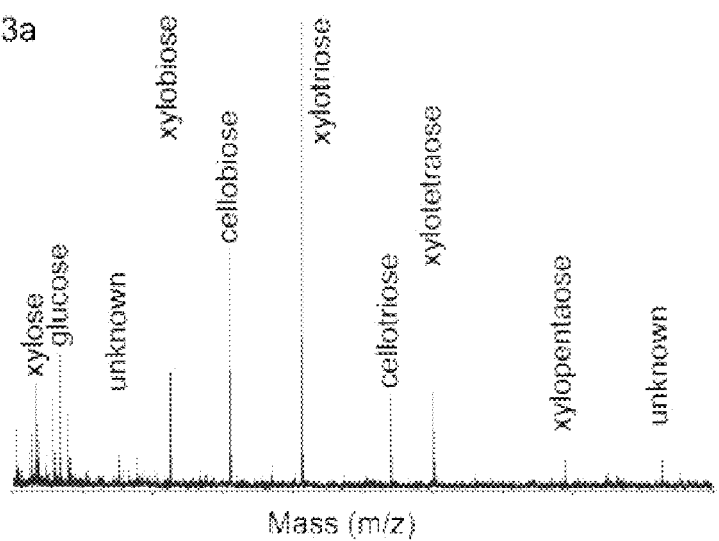
C
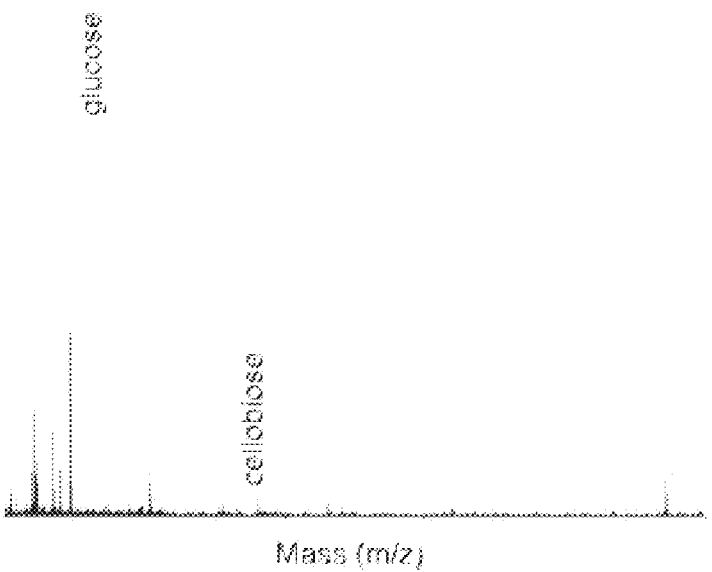
Figure 10 B, C $y[1]$ = cellulose
$y[2]$ = glucose
$y[3]$ = cellobiose
$y[4]$ = cellotriose $dy[1]/d[t] = -(k1 + k2 + k3)\ y[1][t]$
$dy[2]/d[t] = k1\ y[1][t] + k4\ y[3][t] + k5\ y[4][t]$
$dy[3]/d[t] = k2\ y[1][t] + k5\ y[4][t] - k4\ y[3][t]$
$dy[4]/d[t] = k3\ y[1][t] - k5\ y[4][t]$

Figure 12 C

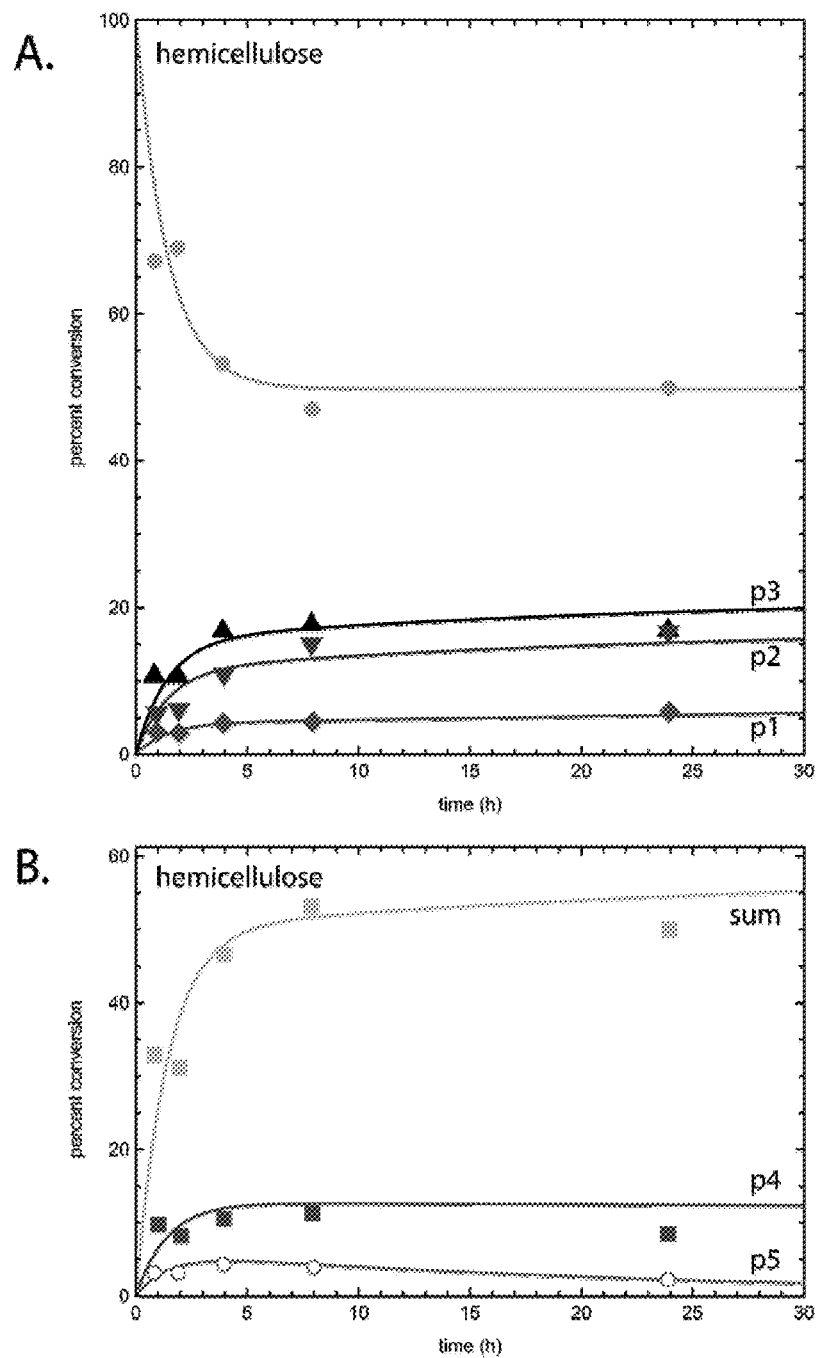
Figure 13 A, B y[1] = hemicellulose
y[2] = pentose
y[3] = pentobiose
y[4] = pentotriose
y[5] = pentotetraose
y[6] = pentopentaose $dy[1]/d[t]$ = −(k1 + k2 + k3 +k4 + k5) y[1][t]
$dy[2]/d[t]$ = k1 y[1][t] + 2 k6 y[3][t] + k7 y[4][t] + k8 y[5][t] + k9 y[6][t]
$dy[3]/d[t]$ = k2 y[1][t] + 2 k10 y[5][t] + k11 y[6][t] + k7 y[4][t] − k6 y[3][t]
$dy[4]/d[t]$ = k3 y[1][t] + k8 y[5][t] + k11 y[6][t] − k7 y[4][t],
$dy[5]/d[t]$ = k4 y[1][t] + k9 y[6][t] − (k8 + k10) y[5][t]
$dy[6]/d[t]$ = k5 y[1][t] − (k9 + k11) y[6][t]

Figure 13 D

SEQUENCE LISTING

<160> NUMBER OF SEQ ID NOS: 7

<210> SEQ ID NO 1
<211> LENGTH: 2295
<212> TYPE: DNA
<213> ORGANISM: Clostridium thermocellum

<400> SEQUENCE: 1

```
atgcgtgata tttcagcaat agatttggtt aaagaaataa aaatcggatg gaatttggga      60
aatactttgg atgctcctac agagactgcc tggggaaatc caaggacaac caaggcaatg     120
atagaaaagg taagggaaat gggctttaat gccgtcagag tgcctgttac ctgggatacg     180
cacatcggac ctgctccgga ctataaaatt gacgaagcat ggctgaacag agttgaggaa     240
gtggtaaact atgttcttga ctgcggtatg tacgcgatca taaatcttca ccatgacaat     300
acatggatta tacctacata tgccaatgag caaaggagta aagaaaaact tgtaaaagtt     360
tgggaacaaa tagcaacccg ttttaaagat tatgacgacc atttgttgtt tgagacaatg     420
aacgaaccga gagaagtagg ttcacctatg gaatggatgg gcggaacgta tgaaaaccga     480
gatgtgataa acagatttaa tttggcggtt gttaatacca tcagagcaag cggcggaaat     540
aacgataaaa gattcatact ggttccgacc aatgcggcaa ccggcctgga tgttgcatta     600
aacgaccttg tcattccgaa caatgacagc agagtcatag tatccataca tgcttattca     660
ccgtatttct ttgctatgga tgtcaacgga acttcatatt ggggaagtga ctatgacaag     720
gcttctctta caagtgaact tgatgctatt tacaacagat ttgtgaaaaa cggaagggct     780
gtaattatcg gagaattcgg aaccattgac aagaacaacc tgtcttcaag ggtggctcat     840
gccgagcact atgcaagaga agcagtttca agaggaattg ctgttttctg gtgggataac     900
ggctattaca atccgggtga tgcagagact tatgcattgc tgaacagaaa aactctctca     960
tggtattatc ctgaaattgt ccaggctctt atgagaggtg ccggcgttga acctttagtt    1020
tcaccgactc ctacacctac attaatgccg acccctcgc ccacggtgac agcaaatatt    1080
```

```
ttgtacggtg acgtaaacgg ggacggaaaa ataaattcta cagactgtac aatgctaaag    1140
agatatattt tgcgtggcat agaagaattc ccaagtccta gcggaattat agccgctgac    1200
gtaaatgcgg atctgaaaat caattccacc gacttggtat tgatgaaaaa atatctactg    1260
cgctcaatag acaaatttcc tgcggaggat tctcaaacac ctgatgaaga caatccgggc    1320
attttgtata acggaagatt cgatttttca gatccgaacg gtccgaaatg cgcctggtcc    1380
ggcagcaatg ttgagctgaa ttttacggc acggaagcaa gtgtgactat caaatccggc    1440
ggtgagaact ggttccaggc tattgtagac ggcaatcctc ttcctccttt ttcggttaac    1500
gctactacct ctaccgtaaa gcttgtaagc ggtcttgcag aaggagctca tcatcttgta    1560
ttgtggaaga ggacagaggc atccttggga gaagttcagt tccttgggtt tgatttggt    1620 tcaggaaagc ttcttgccgc accgaagcct tggaaagaa agattgagtt tatcggagac    1680
tccatcacat gtgcatacgg aaatgaagga acaagcaagg agcagtcttt tacaccgaaa    1740
aatgaaaaca gctatatgtc ttatgcggca attacagccc gtaatttgaa tgcaagtgca    1800
aatatgattg cgtggtccgg aatcggactt accatgaact acggcggagc ccccggacct    1860
cttataatgg accgttatcc ttatacccct ccttacagcg gagtcagatg ggatttttagc    1920 aaatatgtgc ctcaggttgt tgtaatcaat cttggtacca atgatttttc tacatcattt    1980
gcagataaaa caaagtttgt aacggcatat aaaaaccta taagtgaagt tcgcaggaac    2040
tatccggatg cccatatatt ctgctgtgtc ggtccgatgc tttggggaac gggcctggat    2100
ttgtgccgca gttatgttac ggaagttgta aatgattgta acagaagcgg ggattttaaag   2160 gtgtattttg ttgagtttcc gcagcaggac ggaagcaccg gatacggaga agactggcat    2220
ccaagtattg ccacccacca gctgatggct gagcggctta ctgcggaaat aaaaaacaag    2280
cttggatggg tttaa                                                      2295
```

<210> SEQ ID NO 2
<211> LENGTH: 764
<212> TYPE: PRT
<213> ORGANISM: Clostridium thermocellum

<400> SEQUENCE: 2

```
Met Arg Asp Ile Ser Ala Ile Asp Leu Val Lys Glu Ile Lys Ile Gly
 1               5                  10                   15

Trp Asn Leu Gly Asn Thr Leu Asp Ala Pro Thr Glu Thr Ala Trp Gly
                20                  25                  30

Asn Pro Arg Thr Thr Lys Ala Met Ile Glu Lys Val Arg Glu Met Gly
            35                  40                  45

Phe Asn Ala Val Arg Val Pro Val Thr Trp Asp Thr His Ile Gly Pro
        50                  55                  60

Ala Pro Asp Tyr Lys Ile Asp Glu Ala Trp Leu Asn Arg Val Glu Glu
65                  70                  75                  80

Val Val Asn Tyr Val Leu Asp Cys Gly Met Tyr Ala Ile Ile Asn Leu
                85                  90                  95

His His Asp Asn Thr Trp Ile Ile Pro Thr Tyr Ala Asn Glu Gln Arg
            100                 105                 110

Ser Lys Glu Lys Leu Val Lys Val Trp Glu Gln Ile Ala Thr Arg Phe
        115                 120                 125

Lys Asp Tyr Asp Asp His Leu Leu Phe Glu Thr Met Asn Glu Pro Arg
    130                 135                 140

Glu Val Gly Ser Pro Met Glu Trp Met Gly Gly Thr Tyr Glu Asn Arg
```

```
            145                 150                 155                 160
        Asp Val Ile Asn Arg Phe Asn Leu Ala Val Val Asn Thr Ile Arg Ala
                        165                 170                 175

Ser Gly Gly Asn Asn Asp Lys Arg Phe Ile Leu Val Pro Thr Asn Ala
                        180                 185                 190

Ala Thr Gly Leu Asp Val Ala Leu Asn Asp Leu Val Ile Pro Asn Asn
                        195                 200                 205

Asp Ser Arg Val Ile Val Ser Ile His Ala Tyr Ser Pro Tyr Phe Phe
                    210                 215                 220

Ala Met Asp Val Asn Gly Thr Ser Tyr Trp Gly Ser Asp Tyr Asp Lys
        225                 230                 235                 240

Ala Ser Leu Thr Ser Glu Leu Asp Ala Ile Tyr Asn Arg Phe Val Lys
                        245                 250                 255

Asn Gly Arg Ala Val Ile Ile Gly Glu Phe Gly Thr Ile Asp Lys Asn
                        260                 265                 270

Asn Leu Ser Ser Arg Val Ala His Ala Glu His Tyr Ala Arg Glu Ala
                    275                 280                 285

Val Ser Arg Gly Ile Ala Val Phe Trp Trp Asp Asn Gly Tyr Tyr Asn
                290                 295                 300

Pro Gly Asp Ala Glu Thr Tyr Ala Leu Leu Asn Arg Lys Thr Leu Ser
        305                 310                 315                 320

Trp Tyr Tyr Pro Glu Ile Val Gln Ala Leu Met Arg Gly Ala Gly Val
                        325                 330                 335

Glu Pro Leu Val Ser Pro Thr Pro Thr Pro Thr Leu Met Pro Thr Pro
                    340                 345                 350

Ser Pro Thr Val Thr Ala Asn Ile Leu Tyr Gly Asp Val Asn Gly Asp
                    355                 360                 365

Gly Lys Ile Asn Ser Thr Asp Cys Thr Met Leu Lys Arg Tyr Ile Leu
                    370                 375                 380

Arg Gly Ile Glu Glu Phe Pro Ser Pro Ser Gly Ile Ile Ala Ala Asp
        385                 390                 395                 400

Val Asn Ala Asp Leu Lys Ile Asn Ser Thr Asp Leu Val Leu Met Lys
                        405                 410                 415

Lys Tyr Leu Leu Arg Ser Ile Asp Lys Phe Pro Ala Glu Asp Ser Gln
                        420                 425                 430

Thr Pro Asp Glu Asp Asn Pro Gly Ile Leu Tyr Asn Gly Arg Phe Asp
                        435                 440                 445

Phe Ser Asp Pro Asn Gly Pro Lys Cys Ala Trp Ser Gly Ser Asn Val
                    450                 455                 460

Glu Leu Asn Phe Tyr Gly Thr Glu Ala Ser Val Thr Ile Lys Ser Gly
        465                 470                 475                 480

Gly Glu Asn Trp Phe Gln Ala Ile Val Asp Gly Asn Pro Leu Pro Pro
                        485                 490                 495

Phe Ser Val Asn Ala Thr Thr Ser Thr Val Lys Leu Val Ser Gly Leu
                    500                 505                 510

Ala Glu Gly Ala His His Leu Val Leu Trp Lys Arg Thr Glu Ala Ser
                    515                 520                 525

Leu Gly Glu Val Gln Phe Leu Gly Phe Asp Phe Gly Ser Gly Lys Leu
                    530                 535                 540

Leu Ala Ala Pro Lys Pro Leu Glu Arg Lys Ile Glu Phe Ile Gly Asp
        545                 550                 555                 560

Ser Ile Thr Cys Ala Tyr Gly Asn Glu Gly Thr Ser Lys Glu Gln Ser
                        565                 570                 575
```

```
Phe Thr Pro Lys Asn Glu Asn Ser Tyr Met Ser Tyr Ala Ala Ile Thr
            580                 585                 590

Ala Arg Asn Leu Asn Ala Ser Ala Asn Met Ile Ala Trp Ser Gly Ile
        595                 600                 605

Gly Leu Thr Met Asn Tyr Gly Gly Ala Pro Pro Leu Ile Met Asp
    610                 615                 620

Arg Tyr Pro Tyr Thr Leu Pro Tyr Ser Gly Val Arg Trp Asp Phe Ser
625                 630                 635                 640

Lys Tyr Val Pro Gln Val Val Ile Asn Leu Gly Thr Asn Asp Phe
                645                 650                 655

Ser Thr Ser Phe Ala Asp Lys Thr Lys Phe Val Thr Ala Tyr Lys Asn
            660                 665                 670

Leu Ile Ser Glu Val Arg Arg Asn Tyr Pro Asp Ala His Ile Phe Cys
        675                 680                 685

Cys Val Gly Pro Met Leu Trp Gly Thr Gly Leu Asp Leu Cys Arg Ser
    690                 695                 700

Tyr Val Thr Glu Val Val Asn Asp Cys Asn Arg Ser Gly Asp Leu Lys
705                 710                 715                 720

Val Tyr Phe Val Glu Phe Pro Gln Gln Asp Gly Ser Thr Gly Tyr Gly
                725                 730                 735

Glu Asp Trp His Pro Ser Ile Ala Thr His Gln Leu Met Ala Glu Arg
            740                 745                 750

Leu Thr Ala Glu Ile Lys Asn Lys Leu Gly Trp Val
        755                 760
```

<210> SEQ ID NO 3
<211> LENGTH: 1014
<212> TYPE: DNA
<213> ORGANISM: Clostridium thermocellum

<400> SEQUENCE: 3

```
ggcatgcgtg atatttcagc aatagatttg gttaaagaaa taaaaatcgg atggaatttg      60
ggaaatactt tggatgctcc tacagagact gcctggggaa atccaaggac aaccaaggca     120
atgatagaaa aggtaaggga atgggctttt aatgccgtca gagtgcctgt tacctgggat     180
acgcacatcg gacctgctcc ggactataaa attgacgaag catggctgaa cagagttgag     240
gaagtggtaa actatgttct tgactgcggt atgtacgcga tcataaatgt tcaccatgac     300
aatacatgga ttatacctac atatgccaat gagcaaagga gtaaagaaaa acttgtaaaa     360
gtttgggaac aaatagcaac ccgttttaaa gattatgacg accatttgtt gtttgagaca     420
atgaacgaac cgagagaagt aggttcacct atggaatgga tgggcggaac gtatgaaaac     480
cgagatgtga taaacagatt taatttggcg gttgttaata ccatcagagc aagcggcgga     540
aataacgata aagattcat actggttccg accaatgcgg caaccggcct ggatgttgca     600
ttaaacgacc ttgtcattcc gaacaatgac agcagagtca tagtatccat acatgcttat     660
tcaccgtatt tcttggctat ggatgtcaac ggaacttcat attggggaag tgactatgac     720
aaggcttctc ttacaagtga acttgatgct atttacaaca gatttgtgaa aaacggaagg     780
gctgtaatta tcggagaatt cggaaccatt gacaagaaca acctgtcttc aagggtggct     840
catgccgagc actatgcaag agaagcagtt tcaagaggaa ttgctgtttt ctggtgggat     900
aacggctatt acaatccggg tgatgcagag acttatgcat tgctgaacag aaaaactctc     960
tcatggtatt atcctgaaat tgtccaggct cttatgagag gtgccggcgt ttaa          1014
```

<210> SEQ ID NO 4
<211> LENGTH: 337
<212> TYPE: PRT
<213> ORGANISM: Clostridium thermocellum

<400> SEQUENCE: 4

Gly Met Arg Asp Ile Ser Ala Ile Asp Leu Val Lys Glu Ile Lys Ile
1               5                   10                  15

Gly Trp Asn Leu Gly Asn Thr Leu Asp Ala Pro Thr Glu Thr Ala Trp
            20                  25                  30

Gly Asn Pro Arg Thr Thr Lys Ala Met Ile Glu Lys Val Arg Glu Met
        35                  40                  45

Gly Phe Asn Ala Val Arg Val Pro Val Thr Trp Asp Thr His Ile Gly
    50                  55                  60

Pro Ala Pro Asp Tyr Lys Ile Asp Glu Ala Trp Leu Asn Arg Val Glu
65                  70                  75                  80

Glu Val Val Asn Tyr Val Leu Asp Cys Gly Met Tyr Ala Ile Ile Asn
                85                  90                  95

Val His His Asp Asn Thr Trp Ile Ile Pro Thr Tyr Ala Asn Glu Gln
            100                 105                 110

Arg Ser Lys Glu Lys Leu Val Lys Val Trp Glu Gln Ile Ala Thr Arg
        115                 120                 125

Phe Lys Asp Tyr Asp Asp His Leu Leu Phe Glu Thr Met Asn Glu Pro
    130                 135                 140

Arg Glu Val Gly Ser Pro Met Glu Trp Met Gly Gly Thr Tyr Glu Asn
145                 150                 155                 160

Arg Asp Val Ile Asn Arg Phe Asn Leu Ala Val Val Asn Thr Ile Arg
                165                 170                 175

Ala Ser Gly Gly Asn Asn Asp Lys Arg Phe Ile Leu Val Pro Thr Asn
            180                 185                 190

Ala Ala Thr Gly Leu Asp Val Ala Leu Asn Asp Leu Val Ile Pro Asn
        195                 200                 205

Asn Asp Ser Arg Val Ile Val Ser Ile His Ala Tyr Ser Pro Tyr Phe
    210                 215                 220

Phe Ala Met Asp Val Asn Gly Thr Ser Tyr Trp Gly Ser Asp Tyr Asp
225                 230                 235                 240

Lys Ala Ser Leu Thr Ser Glu Leu Asp Ala Ile Tyr Asn Arg Phe Val
                245                 250                 255

Lys Asn Gly Arg Ala Val Ile Ile Gly Glu Phe Gly Thr Ile Asp Lys
            260                 265                 270

Asn Asn Leu Ser Ser Arg Val Ala His Ala Glu His Tyr Ala Arg Glu
        275                 280                 285

Ala Val Ser Arg Gly Ile Ala Val Phe Trp Trp Asp Asn Gly Tyr Tyr
    290                 295                 300

Asn Pro Gly Asp Ala Glu Thr Tyr Ala Leu Leu Asn Arg Lys Thr Leu
305                 310                 315                 320

Ser Trp Tyr Tyr Pro Glu Ile Val Gln Ala Leu Met Arg Gly Ala Gly
                325                 330                 335

Val

<210> SEQ ID NO 5
<211> LENGTH: 1674
<212> TYPE: DNA
<213> ORGANISM: Artificial Sequence
<220> FEATURE:

<223> OTHER INFORMATION: Coding sequence for artificial fusion protein
made from three separate clostridium thermocellum amino acid
sequences.

<400> SEQUENCE: 5

| | | | | | |
|---|---|---|---|---|---|
| atgggaacaa | agcttttgga | tgcaagcgga | aacgagcttg | taatgagggg | catgcgtgat | 60 |
| atttcagcaa | tagatttggt | taaagaaata | aaaatcggat | ggaatttggg | aaatactttg | 120 |
| gatgctccta | cagagactgc | ctggggaaat | ccaaggacaa | ccaaggcaat | gatagaaaag | 180 |
| gtaagggaaa | tgggctttaa | tgccgtcaga | gtgcctgtta | cctgggatac | gcacatcgga | 240 |
| cctgctccgg | actataaaat | tgacgaagca | tggctgaaca | gagttgagga | agtggtaaac | 300 |
| tatgttcttg | actgcggtat | gtacgcgatc | ataaatcttc | accatgacaa | tacatggatt | 360 |
| atacctacat | atgccaatga | gcaaaggagt | aagaaaaaac | ttgtaaaagt | ttgggaacaa | 420 |
| atagcaaccc | gttttaaaga | ttatgacgac | catttgttgt | tgagacaat | gaacgaaccg | 480 |
| agagaagtag | gttcacctat | ggaatggatg | ggcggaacgt | atgaaaaccg | agatgtgata | 540 |
| aacagattta | atttggcggt | tgttaatacc | atcagagcaa | gcggcggaaa | taacgataaa | 600 |
| agattcatac | tggttccgac | caatgcggca | accggcctgg | atgttgcatt | aaacgacctt | 660 |
| gtcattccga | caatgacag | cagagtcata | gtatccatac | atgcttattc | accgtatttc | 720 |
| tttgctatgg | atgtcaacgg | aacttcatat | tggggaagtg | actatgacaa | ggcttctctt | 780 |
| acaagtgaac | ttgatgctat | ttacaacaga | tttgtgaaaa | acggaagggc | tgtaattatc | 840 |
| ggagaattcg | gaaccattga | caagaacaac | ctgtcttcaa | gggtggctca | tgccgagcac | 900 |
| tatgcaagag | aagcagtttc | aagaggaatt | gctgttttct | ggtgggataa | cggctattac | 960 |
| aatccgggtg | atgcagagac | ttatgcattg | ctgaacagaa | aaactctctc | atggtattat | 1020 |
| cctgaaattg | tccaggctct | tatgagaggt | gccggcgttg | aaagtttaaa | cgcgactccc | 1080 |
| actaaaggtg | ccactcctac | caatacggcg | actccgacta | agtcggcaac | ggcaacgccc | 1140 |
| actcgcccca | gcgtaccgac | caatactccg | actaataccc | cggcgaacac | cccagtaagc | 1200 |
| ggtaacctga | aggttgaatt | ttataactcc | aacccaagcg | cacacaacgaa | tagcatcaat | 1260 |
| ccgcagttca | aagtcacgaa | cactggcagt | tcagctatcg | atctgtcgaa | actgaccctt | 1320 |
| cgttactact | atacggttga | tggccaaaaa | gatcagacct | tttggtgcga | ccatgcagca | 1380 |
| atcatcggta | gcaatggttc | ttataacggc | attacttcta | atgtaaaagg | caccttttgtg | 1440 |
| aagatgtcaa | gtagcaccaa | caatgctgat | acctacctgg | aaattagctt | cacgggtggc | 1500 |
| acacttgaac | caggagccca | cgtccagatc | cagggccgtt | ttgcgaaaaa | cgattggagc | 1560 |
| aactatacgc | aatcaaacga | ttatagtttc | aaaagcgcgt | ctcaattcgt | agaatgggat | 1620 |
| caggtgaccg | catatttgaa | cggagtgctg | gtttggggga | agaaccagg | atag | 1674 |

<210> SEQ ID NO 6
<211> LENGTH: 557
<212> TYPE: PRT
<213> ORGANISM: Artificial Sequence
<220> FEATURE:
<223> OTHER INFORMATION: Sequence for artificial fusion protein made
from three separate clostridium thermocellum amino acid sequences.

<400> SEQUENCE: 6

Met Gly Thr Lys Leu Leu Asp Ala Ser Gly Asn Glu Leu Val Met Arg
1               5                   10                  15

Gly Met Arg Asp Ile Ser Ala Ile Asp Leu Val Lys Glu Ile Lys Ile
            20                  25                  30

-continued

```
Gly Trp Asn Leu Gly Asn Thr Leu Asp Ala Pro Thr Glu Thr Ala Trp
         35                  40                  45
Gly Asn Pro Arg Thr Thr Lys Ala Met Ile Glu Lys Val Arg Glu Met
 50                  55                  60
Gly Phe Asn Ala Val Arg Val Pro Val Thr Trp Asp Thr His Ile Gly
 65                  70                  75                  80
Pro Ala Pro Asp Tyr Lys Ile Asp Glu Ala Trp Leu Asn Arg Val Glu
                 85                  90                  95
Glu Val Val Asn Tyr Val Leu Asp Cys Gly Met Tyr Ala Ile Ile Asn
                100                 105                 110
Leu His His Asp Asn Thr Trp Ile Ile Pro Thr Tyr Ala Asn Glu Gln
        115                 120                 125
Arg Ser Lys Glu Lys Leu Val Lys Val Trp Glu Gln Ile Ala Thr Arg
130                 135                 140
Phe Lys Asp Tyr Asp Asp His Leu Leu Phe Glu Thr Met Asn Glu Pro
145                 150                 155                 160
Arg Glu Val Gly Ser Pro Met Glu Trp Met Gly Gly Thr Tyr Glu Asn
                165                 170                 175
Arg Asp Val Ile Asn Arg Phe Asn Leu Ala Val Val Asn Thr Ile Arg
                180                 185                 190
Ala Ser Gly Gly Asn Asn Asp Lys Arg Phe Ile Leu Val Pro Thr Asn
        195                 200                 205
Ala Ala Thr Gly Leu Asp Val Ala Leu Asn Asp Leu Val Ile Pro Asn
210                 215                 220
Asn Asp Ser Arg Val Ile Val Ser Ile His Ala Tyr Ser Pro Tyr Phe
225                 230                 235                 240
Phe Ala Met Asp Val Asn Gly Thr Ser Tyr Trp Gly Ser Asp Tyr Asp
                245                 250                 255
Lys Ala Ser Leu Thr Ser Glu Leu Asp Ala Ile Tyr Asn Arg Phe Val
                260                 265                 270
Lys Asn Gly Arg Ala Val Ile Ile Gly Glu Phe Gly Thr Ile Asp Lys
        275                 280                 285
Asn Asn Leu Ser Ser Arg Val Ala His Ala Glu His Tyr Ala Arg Glu
290                 295                 300
Ala Val Ser Arg Gly Ile Ala Val Phe Trp Trp Asp Asn Gly Tyr Tyr
305                 310                 315                 320
Asn Pro Gly Asp Ala Glu Thr Tyr Ala Leu Leu Asn Arg Lys Thr Leu
                325                 330                 335
Ser Trp Tyr Tyr Pro Glu Ile Val Gln Ala Leu Met Arg Gly Ala Gly
                340                 345                 350
Val Glu Ser Leu Asn Ala Thr Pro Thr Lys Gly Ala Thr Pro Thr Asn
        355                 360                 365
Thr Ala Thr Pro Thr Lys Ser Ala Thr Ala Thr Pro Thr Arg Pro Ser
370                 375                 380
Val Pro Thr Asn Thr Pro Thr Asn Thr Pro Ala Asn Thr Pro Val Ser
385                 390                 395                 400
Gly Asn Leu Lys Val Glu Phe Tyr Asn Ser Asn Pro Ser Asp Thr Thr
                405                 410                 415
Asn Ser Ile Asn Pro Gln Phe Lys Val Thr Asn Thr Gly Ser Ser Ala
                420                 425                 430
Ile Asp Leu Ser Lys Leu Thr Leu Arg Tyr Tyr Tyr Thr Val Asp Gly
        435                 440                 445
Gln Lys Asp Gln Thr Phe Trp Cys Asp His Ala Ala Ile Ile Gly Ser
```

```
                    450                       455                       460
Asn Gly Ser Tyr Asn Gly Ile Thr Ser Asn Val Lys Gly Thr Phe Val
465                     470                     475                     480

Lys Met Ser Ser Ser Thr Asn Asn Ala Asp Thr Tyr Leu Glu Ile Ser
                485                     490                     495

Phe Thr Gly Gly Thr Leu Glu Pro Gly Ala His Val Gln Ile Gln Gly
                500                     505                     510

Arg Phe Ala Lys Asn Asp Trp Ser Asn Tyr Thr Gln Ser Asn Asp Tyr
            515                     520                     525

Ser Phe Lys Ser Ala Ser Gln Phe Val Glu Trp Asp Gln Val Thr Ala
            530                     535                     540

Tyr Leu Asn Gly Val Leu Val Trp Gly Lys Glu Pro Gly
545                     550                     555

<210> SEQ ID NO 7
<211> LENGTH: 15
<212> TYPE: PRT
<213> ORGANISM: Clostridium thermocellum

<400> SEQUENCE: 7

Thr Val Thr Ala Gly Thr Ala Ala Ala Leu Ala Ala Thr Ala Leu
1               5                   10                  15
```

MULTIFUNCTIONAL CELLULASE AND HEMICELLULASE

CROSS-REFERENCE TO RELATED APPLICATIONS

This application claims the benefit of U.S. provisional Application No. 61/703,063, filed Sep. 19, 2012, which is incorporated herein by reference for all purposes.

STATEMENT REGARDING FEDERALLY SPONSORED RESEARCH

This invention was made with government support under DE-FC02-07ER64494 awarded by the US Department of Energy and GM094584 awarded by the National Institutes of Health. The government has certain rights in the invention.

BACKGROUND

Conversion of the insoluble cellulose and hemicellulose polymers found in plant biomass into soluble sugars represents a major bottleneck for the biofuel industry. In order to accomplish this conversion, chemical pretreatment and enzyme hydrolysis are usually required.

Among chemical pretreatments, ammonia fiber expansion (AFEX) alkaline pretreatment has many advantages, such as (1) being a dry to dry process that does not produce a wash or liquid stream, (2) producing a chemically similar biomass composition after pretreatment, and (3) resulting in cleaved lignin-carbohydrate complexes without physically extracting hemicelluloses or lignin into separate process streams. Because alkaline pretreatments retain all constituent fractions of biomass, these pretreatments must be paired with the use of a complex mixture of cellulases and hemicellulases to achieve effective hydrolysis. It would be desirable to decrease the number of enzymes required to provide high yield conversion of polysaccharides present in AFEX-pretreated biomass.

Furthermore, a new variant chemical pretreatment called extractive AFEX (E-AFEX) leads to the production of cellulose III, an unnatural form of cellulose (Chundawat, et al., 2011). The extractive AFEX process not only generates cellulose III as a potentially more easily hydrolyzed allomorph, but also partially removes lignin. Both of these beneficial effects should promote enzymatic processing. Enzyme cocktails which hydrolyze cellulose III may have unique complementarity and thus corresponding utility when combined with the E-AFEX process.

In nature, the complex ultra-structure of the plant cell wall requires the participation of a mixture of many different enzymes to efficiently carry out the conversion of biopolymers into soluble sugars. This mixture is called an enzyme cocktail. An enzyme cocktail simultaneously provides cellulase, xylanase, mannanase, and enzymes having other catalytic activities. Cocktails of enzymes that have high hydrolyzing efficiency for either AFEX treated or extractive AFEX (E-AFEX) treated biomass will have great potential in the biofuel industry.

Chemical pretreatments and enzymes must be used together in order to achieve a high-yield deconstruction of biomass into fermentable sugars. As many as 18 different purified enzymes may be required to give a high yield conversion of AFEX pretreated biomass into soluble sugars, because AFEX pretreatment does not destroy the many types of bonds found in hemicellulose. Approaches that result in a reduced number of enzymes required for an efficient biomass hydrolysis would be beneficial to the biofuel industry, because it would be easier to manufacture a smaller number of enzymes, and the total weight of enzyme required may also be decreased.

One way to simplify the composition of enzyme cocktails is to use multifunctional enzymes, whereby a single multifunctional enzyme can replace two or more monofunctional enzymes in the cocktail. As a result of such substitutions, a less complex enzyme cocktail containing fewer enzymes may be used.

Accordingly, there is a need in the art for a multifunctional enzyme which can hydrolyze the three major materials of plant cell walls: cellulose, xylan, and mannan. Such a multifunctional enzyme could replace two or more enzymes in a conventional enzyme cocktail, while providing advantages in specific activity and stability of the cocktail.

BRIEF SUMMARY OF THE INVENTION

In one aspect, the present invention encompasses a multifunctional polypeptide capable of hydrolyzing a cellulosic material, xylan, and mannan. The multifunctional polypeptide comprises the catalytic core (cc) of *Clostridium thermocellum* Cthe_0797 (CelE), a cellulose-specific carbohydrate-binding module (CBM), wherein the CBM is CBM3 of the cellulosome anchoring protein cohesion region (CipA) of *Clostridium thermocellum* (CBM3a), and a linker region interposed between the catalytic domain and the cellulose-specific carbohydrate binding module. In one embodiment, the linker region consists of a 15-40 amino acid sequence.

In certain embodiments, the cellulosic material suitable for being hydrolyzed by the polypeptide is a material selected from the group consisting of filter paper, crystalline cellulose allomorph I, and amorphous cellulose. In some embodiments, the cellulosic material suitable for being hydrolyzed by the polypeptide is cellulose III. In some embodiments, the cellulosic material suitable for being hydrolyzed by the polypeptide is pretreated using acidic, basic, or oxidative pretreatment methods. In some embodiments, the cellulose III suitable for being hydrolyzed by the polypeptide is non-natural cellulose and is produced by extractive ammonia fiber expansion treatment of biomasses.

In some embodiments, the polypeptide is capable of hydrolyzing SIGMACELL, beta-glucan, galactan, galactomannan, and lichenan. In some embodiments, the catalytic reactivity of polypeptide is at least 50% higher than that of the native CelE. In some embodiments, the catalytic reactivity of the polypeptide is at least 1.5 times, preferably at least 2 times, higher than that of the catalytic core (cc) of the native CelE. In some embodiments, the polypeptide is most catalytically reactive at 60° C., and the polypeptide retains at least 50% of its maximal reactivity at 45° C. In some embodiments, the polypeptide is most catalytically reactive at pH 6.0 and the polypeptide retains at least 50% of the maximal activity at pH 4.5. In some embodiments, the polypeptide remains active under a salt concentration of at least 20% (weight per volume).

In some embodiments, the polypeptide comprises the amino acid sequence of the protein CelEcc_CBM3a (SEQ ID NO:6). In some such embodiments, the amino acid sequence of SEQ ID NO:6 is encoded by the nucleotide sequence of SEQ ID NO:5.

In some embodiments, a polypeptide composition that includes the polypeptide as described above can be used for increasing the rate and the extent of fiber digestion in a mammal. In some embodiments, the mammal can be selected from the group consisting of human, cattle, goats, sheep, giraffes, bison, moose, elk, yaks, water buffalo, deer, camels, alpacas, llamas, antelope, pronghorn, nilgai, kangaroo, horse, pig and rabbit.

In a second aspect, the present invention encompasses a method of hydrolyzing a substrate comprising cellulosic materials, xylan, and mannan. The method includes the step of exposing a substrate comprising a cellulosic material, xylan, and mannan to an effective amount of the multifunctional polypeptide as described above, whereby the cellulosic materials, xylan, and mannan in the substrate are at least partially hydrolyzed.

In some embodiments, the cellulosic material is selected from the group consisting of filter paper, crystalline cellulose allomorph I, and amorphous cellulose. In some embodiments, the cellulosic material is cellulose III. In some embodiments, the cellulosic material suitable for the polypeptide is pretreated using acidic, basic, or oxidative pretreatments. In some such embodiments, the cellulose III is non-natural cellulose and is produced by extractive ammonia fiber expansion treatment of biomass.

In some embodiments, one or more of SIGMACELL, beta-glucan, galactan, galactomannan, and lichenan are also hydrolyzed. In some embodiments, the catalytic reactivity of the polypeptide is at least 50% higher than that of the native CelE. In some embodiments, the catalytic reactivity of polypeptide is at least 1.5 times, preferably at least 2 times, higher than that of the catalytic core (cc) of the native CelE. In some embodiments, the polypeptide is most catalytically reactive at 60° C., and the polypeptide retains at least 50% of the maximal reactivity at 45° C. In some embodiments, the polypeptide is most catalytically reactive at pH 6.0 and the peptide retains at least 50% of the maximal activity at pH 4.5. In some embodiments, the polypeptide remains active under a salt concentration of at least 20% (weight per volume).

In some embodiments, the effective amount of the multifunctional polypeptide is in the range of 1-100 mg/g (enzyme/glucan), preferably 1-10 mg/g (enzyme/glucan).

In a third aspect, the present invention encompasses a method of increasing the rate and the extent of fiber digestion in a mammal. The method includes the step of administering to a mammal an effective amount of the multifunctional polypeptide as described above, whereby the cellulosic materials, xylan, and mannan in the fiber consumed by the mammal are at least partially hydrolyzed. In some embodiments, the mammal is selected from the group consisting of human, cattle, goats, sheep, giraffes, bison, moose, elk, yaks, water buffalo, deer, camels, alpacas, llamas, antelope, pronghorn, nilgai, kangaroo, horse, pig and rabbit. In some embodiments, the effective amount of multifunctional polypeptide is in the range of 1-100 mg/g (enzyme/glucan), preferably 1-10 mg/g (enzyme/glucan). In some embodiments, the concentration of the multifunctional polypeptide is in the range of 20-200 nmol/g (enzyme/glucan).

In a fourth aspect, the present invention encompasses a method of making a multifunctional polypeptide. The method includes the step of linking the catalytic core (cc) of *Clostridium thermocellum* Cthe_0797 (CelE) with a cellulose-specific carbohydrate-binding module (CBM) by using a linker region, whereby a linker region is interposed between the catalytic domain and the cellulose-specific carbohydrate binding module, and wherein the CBM is CBM3 of the cellulosome anchoring protein cohesion region (CipA) of *Clostridium thermocellum* (CBM3a).

DESCRIPTION OF THE DRAWINGS

FIG. 2A shows the native CelE gene nucleic acid sequence (SEQ ID NO:1); FIG. 2B shows the native CelE protein amino acid sequence (SEQ ID NO:2).

FIG. 3A shows the CelEcc gene nucleic acid sequence (SEQ ID NO:3); FIG. 3B shows the CelEcc protein amino acid sequence (SEQ ID NO:4).

FIG. 4A shows the CelE_CBM3a gene nucleic acid sequence (SEQ ID NO:5); FIG. 4B shows the CelE_CBM3a protein amino acid sequence (SEQ ID NO:6).

FIG. 10 is a set of diagrams and graphs showing the multifunctional catalytic activity of CelEcc_CBM3a. FIG. 10B is a graph showing the NIMS analysis of the products from the catalytic reaction of CelEcc_CBM3a (Cthe_0797; GH5) with AFEX-switchgrass. FIG. 10C is a graph showing NIMS analysis of the products from the catalytic reaction of BglA (Cthe_0212; GH1) with AFEX-switchgrass as a control experiment.

FIG. 11A is a graph showing the time-dependent catalytic reactions and kinetics of CelB (Cthe_0536) with IL-SG. FIG. 11B is a graph showing the time-dependent catalytic reactions and kinetics of CelEcc_CBM3a (Cthe_0797) with IL-SG.

FIG. 12A is a graph showing time-dependent catalytic reactions and product formation kinetics of CelEcc_CBM3a (Cthe_0797) with cellulose. FIG. 12B is a diagram showing a predictive kinetic scheme for the catalytic reaction between CelEcc_CBM3a (Cthe_0797) and cellulose. FIG. 12C shows the differential equations corresponding to FIG. 12B. These equations are used to perform the analysis of time-dependence of product formation from cellulose hydrolysis.

FIGS. 13A-B are graphs showing time-dependent catalytic reactions and product formation kinetics of CelEcc_CBM3a (Cthe_0797) with hemicellulose. FIG. 13C is a diagram showing a predictive kinetic scheme for the catalytic reaction between CelEcc_CBM3a (Cthe_0797) and hemicellulose. FIG. 13D shows the differential equations corresponding to FIG. 13C. These equations are used to perform the analysis of time-dependence of product formation from hemicellulose hydrolysis.

DESCRIPTION OF THE INVENTION

In General

Figure 1:
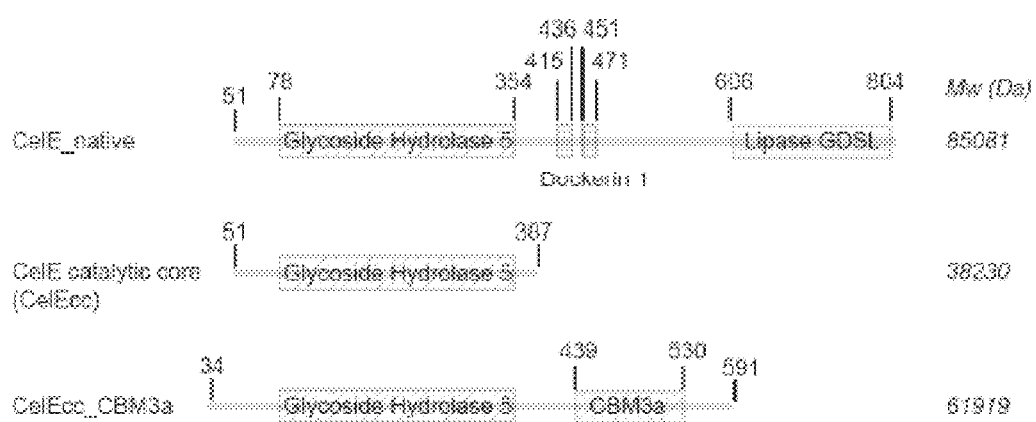
FIG. 1 is a schematic diagram illustrating the domain structures of native CelE, CelEcc, and CelE_CBM3a. Molecular weight (Da) and positions of amino acid residues of each domain relative to CelE sequence (NCBI:gi125973315, incorporated by reference herein) are indicated. Truncation of the N-terminus of each construct (missing the first 30 to 50 residues) is due to the presence of undesirable signal peptide in the reported sequence.

Typical cellulases and hemicellulases can often cleave only one type of glycosidic bond with high specificity. To effectively hydrolyze the ultrastructure of plant cell walls into soluble sugars, a complex combination of enzymes, including multiple cellulases, xylanases, mannanases, etc., is typically required. It would be helpful to use a single multifunctional enzyme capable of substituting for at least two cellulases, xylanases, or mannanases in a hydrolyzing enzyme cocktail.

The inventors have produced a multifunctional enzyme that can hydrolyze three major components of plant cell walls, including cellulosic materials, mannan, and xylan. In one aspect of the invention, the multifunctional enzyme remains catalytically active under harsh environments. Harsh environments include high temperatures (35-60° C.), acidic solution (pH 4.5), and high concentration of salt (at least 20%).

Cellulose III, an unnatural form of cellulose, has been produced through the chemical pretreatment of extractive ammonia fiber expansion (E-AFEX) (Chundawat, et al., 2011). In one embodiment, the present invention provides an enzyme or a polypeptide showing a specific catalytic reactivity with cellulose III.

Compositions of the Present Invention

As used herein, the term "multifunctional" refers to an enzyme or a polypeptide capable of hydrolyzing a cellulosic material, xylan, and mannan.

"Cellulosic materials," as used herein, refers to any material or any combination of materials containing various forms of cellulose. Non-limiting examples of cellulosic materials include filter paper, crystalline cellulose allomorph I, amorphous cellulose, cellulose III, hemicelluloses, corn stover, corn stalks, wheat straw, cereal grain, cotton, and other agricultural residues, and industrial biomass, including miscanthus, switchgrass, hemp, poplar, willow, sorghum, sugarcane, bamboo, and any other cellulose-containing materials.

As used herein, the term "stable" refers to an enzyme or a polypeptide that remains catalytically active hydrolyzing biomass for at least 100 hours.

As used herein, the term "highly reactive" refers to an enzyme or a polypeptide retaining more than 70% of its maximal reactivity.

As used herein, the term "high concentration of salt" refers to a salt having a concentration higher than 20% weight per volume.

As used herein, the term "partially active" refers to an enzyme or peptide retaining at least 50% of its maximal activity.

As used herein, the terms "substrate," "solid substrate," or "insoluble substrate" refer to a material comprising one or more cellulosic materials, xylan, and mannan.

The terms "enzyme," "polypeptide," and "protein," are used interchangeably throughout this disclosure.

The term "linker region" refers to a sequence interposed between the CelEcc and the CBM3a. The molecule is preferably an enzyme or a peptide, and may be of any length that permits the connected sequences to function catalytically. Preferably, the linker region is derived from the CipA (Cthe_3077) protein from Clostridium thermocellum. The linker used in the construct in the Examples is the amino acid sequence right before the CBM3a domain from C. thermocellum CipA (Cthe_3077). The linker includes residues 324-364 of SEQ ID NO:6 (CBM3a includes residues 365-523 of SEQ ID NO:6). This linker region may be susceptible to proteolysis by trypsin-like proteases, which may be a problem in ruminant applications. This problem could be overcome by providing a different amino acid sequence, preferably one lacking Arg and Lys residues, or by a sequence that supports glycosylation.

The natural protein CelR provides an example of a useful alternative linker region. The natural domain structure of CelR is GH9-CBM3a-Dockerin-Dockerin. The form that the inventors described in a previous patent application (U.S. Patent Publication No. 2010/0304405, incorporated by reference herein) was engineered to have the format of GH9-CBM3a-CBM3a, where the second CBM3a was from the CipA gene, which is the same CBM3a that is disclosed herein as linked to CelEcc. The first CBM3 domain also has a linker, and the linker is not hydrolyzed by protease-rich rumen fluid. The short sequence of this linker, which includes residues 178 to 193 of the CelR gene (Cthe_0578) (TVTAGTAAA-LAATAL (SEQ ID NO:7)), still allows the CelR catalytic domain to function. Other amino acid sequences may also be suitable for use as a linker region. Suitable amino acid sequences may include 5-150 residues, preferably 10-50 residues, most preferably 15-40 residues.

Substrates of cellulosic materials, xylan, and mannan used in the disclosed methods may first be pretreated. The pretreatment process may include any conventional pretreatment methods, including without limitation acidic, basic, or oxidative methods. Preferably, the pretreatment process may be an ammonia fiber expansion (AFEX) process. Most preferably, the pretreatment process may be an extractive ammonia fiber expansion (E-AFEX) process.

In one embodiment of the invention, Clostridium thermocellum Cthe_0797, also called CelE, is used as a multifunctional polysaccharide-degrading enzyme. CelE was described in U.S. Patent Publication No. 2010/0304405, which is incorporated by reference herein. As shown in FIG. 1, the native CelE is composed of four domains, including one glycoside hydrolase 5 (GH5), two dockerin type 1 domains, and a lipase GDSL domain. The amino acid positions where these domains begin and end are indicated in FIG. 1. Native CelE is capable of hydrolyzing cellulosic materials, including filter paper, crystalline cellulose allomorph I, amorphous cellulose, and others. CelE can also hydrolyze mannan, galactomannan, xylan, and lichenan. With this broad catalytic specificity, CelE has potential utility as a dominant enzyme in new enzyme cocktails for use in biomass hydrolysis.

In another embodiment, truncation of the natural dockerin domain from the C-terminus of the native CelE increases its stability upon heterologous expression, leading to the production of the catalytic core (cc) of the native CelE (CelEcc). As shown in FIG. 1, CelEcc includes only one glycoside hydrolase 5 (GH5) domain. CelEcc is capable of hydrolyzing cellulosic materials, including filter paper, crystalline cellulose allomorph I, amorphous cellulose, and others. CelEcc can also hydrolyze mannan, galactomannan, xylan, and lichenan.

Further, by applying an engineered fusion domain approach, such as that disclosed in U.S. Patent Publication No. 2010/0304405 (incorporated by reference herein), an enzyme with improved catalytic reactivity was produced by introducing a linker region from one protein or polypeptide and a cellulose-specific carbohydrate-binding module from another different protein or polypeptide. CBM3a was used here as the cellulose-specific carbohydrate-binding module, as it has been reported to specifically bind to a planar cellulose surface. CBM3a is encoded as an internal domain of the cellulosome anchoring protein (CipA; Cthe_3077) of *Clostridium thermocellum*. This portion of the protein has been incorporated into the engineered fusion domain approach by PCR amplification and cloning.

As shown in FIG. 1, the resulting fusion enzyme, CelEcc_CBM3a, includes the catalytic core of native CelE (CelEcc) having one single glycoside hydrolase 5 (GH5) domain, one cellulose-specific carbohydrate-binding module (CBM3a), and a linker region (not labeled) connecting CelEcc and CBM3a. This construct is created to optimize the performance of the enzyme, and the replacement of the dockerin domain with the CBM3a domain abrogates the need for a cellulosomal attachment to obtain maximal catalytic activity from CelEcc_CBM3a on solid substrates. Following similar strategies, one might wish to use other substrate-specific carbohydrate-binding modules instead of CBM3a to create enzymes targeting the corresponding substrates. The resulting enzymes might be specific to beta-glucan, galactan, mannan, galactomannan, xylan, lichenan, cellulosic materials, or any other polysaccharide included in biomass.

Native CelE, the catalytic core of native CelE (CelEcc), and the engineered construct of CelEcc_CBM3a may be expressed in any manner known to those skilled in the art, including utilizing an *Escherichia coli* expression system by cloning corresponding coding sequences into *E. coli* expression vector following a similar method and process as described in U.S. Patent Publication No. 2010/0304405, which is incorporated by reference herein. Gene and protein sequences of native CelE, CelEcc, and CelEcc-CBM3a are shown in FIG. 2, FIG. 3, and FIG. 4, respectively.

Figure 5:
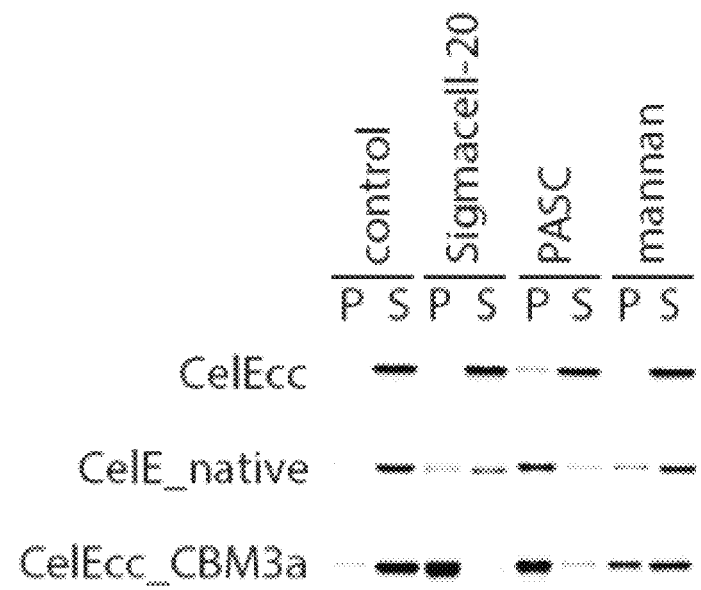
FIG. 5 is a graph of sodium dodecyl sulfate polyacryamide gel electrophoresis (SDS-PAGE) analysis showing the binding affinity for insoluble polysaccharides assessed by pull-down assay for three different constructs of CelE.

In one embodiment of the invention, the engineered construct of CelEcc_CBM3a shows a much stronger binding affinity to insoluble polysaccharide substrates than native CelE and CelEcc. FIG. 5 shows a comparison of binding affinity of CelE, CelEcc, and CelEcc_CBM3a with the substrates of crystalline cellulose (SIGMACELL-20), phosphoric acid amorphous cellulose (PASC) and mannan. As depicted in FIG. 5, the bound and unbound fraction are indicated as pellet (P) and supernatant (S), respectively. As expected, native CelE, which is a cellulosomal protein lacking a carbohydrate-binding module (CBM) domain, shows only weak binding affinities to all three substrates of SIGMACELL-20, PASC, and mannan. The catalytic core of native CelE (CelEcc) does not bind to the substrates of SIGMACELL-20 and mannan and CelEcc only weakly binds to PASC, compared to a control. In contrast, the engineered construct of CelEcc_CBM3a shows a much stronger binding affinity to the substrates of SIGMACELL-20, PASC, and mannan than native CelE and CelEcc. Fusion of a carbohydrate-binding module (CBM3a) onto the catalytic core of native CelE (CelEcc) appears to increase the binding affinity of the resulting enzyme with solid substrates, thus potentially improving the catalytic reactivity of the enzyme.

In another embodiment of the invention, high pressure liquid chromatography (HPLC) is used to identify (and optionally quantify) soluble sugars and the hydrolysis products of insoluble substrates following enzyme catalysis. For example, HPLC assays of the hydrolysis products demonstrate that the catalysis of CelE produces cellotriose, xylotriose, and mannotriose from oligosaccharide cellohexaose, xylohexaose, and mannohexaose, respectively, as the corresponding major soluble products.

Figure 6:
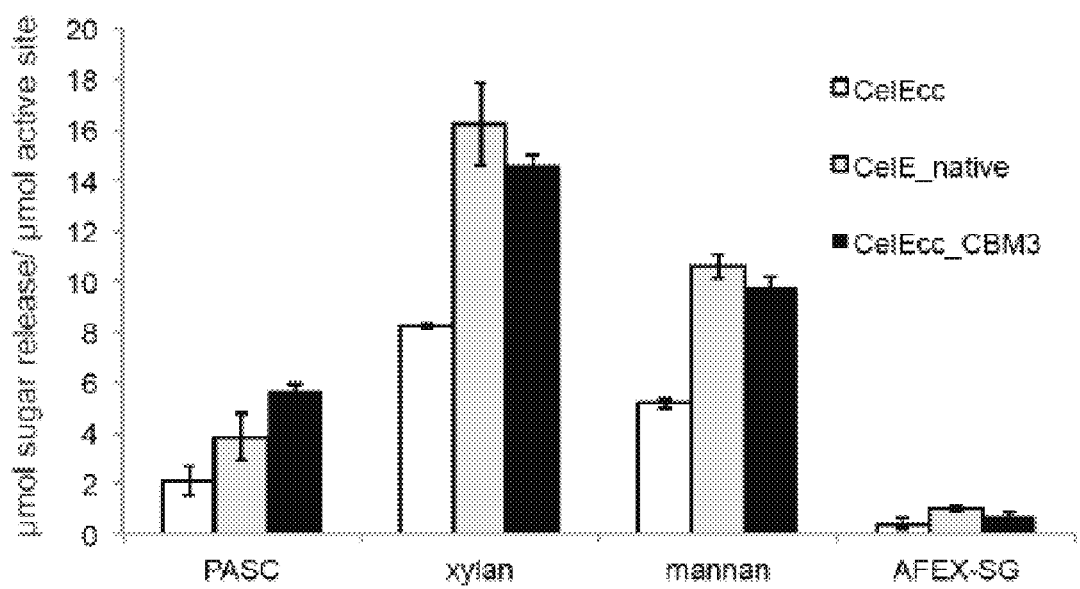
FIG. 6 is a diagram demonstrating cellulase and hemicellulase activity of CelE, native CelE, and CelEcc_CBM3a. Hydrolytic activity of CelEcc, native CelE, and CelEcc_CBM3 in μmol sugar release per μmol of active site are shown on phosphoric acid swollen cellulose (PASC), xylan, mannan and AFEX-pretreated switchgrass (AFEX-SG). Reaction was carried out at 8 mg/g enzyme to glucan for 20 hours at 60° C. DNS measurement was performed to determine the reducing end sugar products released in each reaction.

In one preferred embodiment of the invention, fusion of a carbohydrate-binding module (CBM3a) onto the catalytic core of native CelE (CelEcc) has greatly increased the catalytic reactivity of the resulting enzyme (CelEcc_CBM3a) with cellulosic materials. FIG. 6 demonstrates that native CelE, CelEcc, and CelEcc_CBM3a have different rates and relative activities for hydrolyzing insoluble substrates. As shown in FIG. 6, the engineered construct of CelEcc_CBM3a has a catalytic reactivity with phosphoric acid amorphous cellulose (PASC) of at least 50% higher than that of native CelE. The engineered construct of CelEcc_CBM3a has a catalytic reactivity with phosphoric acid amorphous cellulose (PASC) at least three times over that of CelEcc. While CelEcc_CBM3a shows a comparable reactivity with xylan and mannan to that of native CelE, the presence of CBM3a increases the catalytic reactivity by at least 1.5 times, preferably 2 times compared with that of CelEcc. In another embodiment of the reaction, CelEcc_CBM3a was shown to hydrolyze SIGMACELL, filter paper, beta-glucan, galactan, mannan, galactomannan, xylan, and lichenan.

Figure 7:
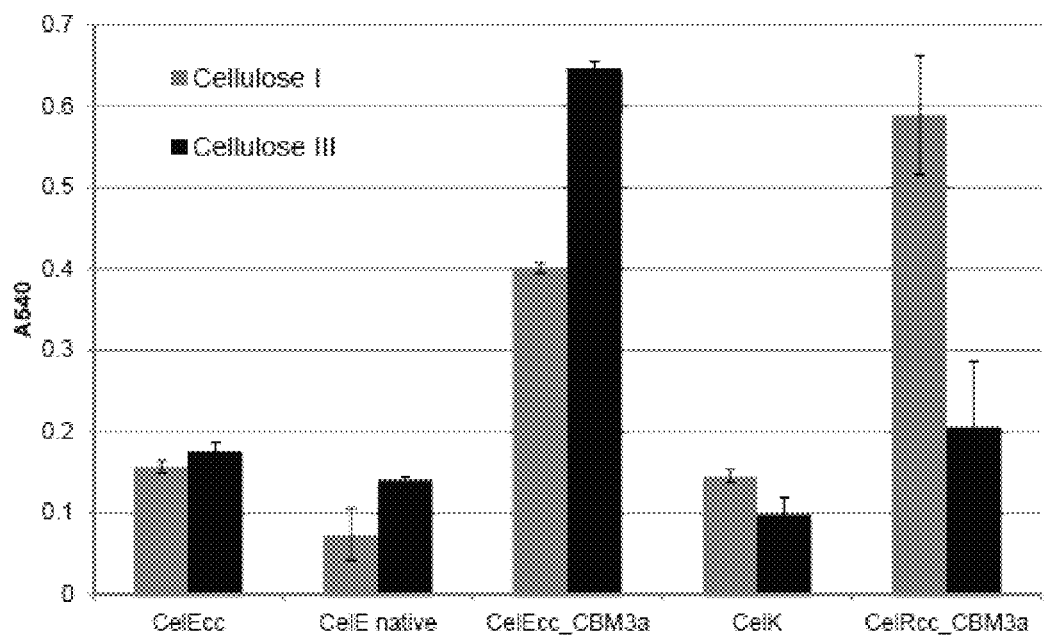
FIG. 7 is a diagram showing a catalytic activity comparison of CelEcc, CelE native, CelEcc_CBM3a, CelK, and CelRcc_CBM3a with either cellulose I (SIGMACELL-20) or cellulose III prepared from SIGMACELL-20 by extractive AFEX.

Further, in another preferred embodiment of the invention, the engineered construct of CelEcc_CBM3a shows significant improvement of catalytic reactivity with specific substrates such as cellulose I and cellulose III. FIG. 7 depicts a catalytic activity comparison of CelEcc, CelE native, CelEcc_CBM3a, CelK, and CelRcc_CBM3a with either cellulose I (SIGMACELL-20) or cellulose III prepared from SIGMACELL-20 by extractive AFEX. The creation and utility of CelKcc and CelRcc_CBM3a was described in U.S. Patent Publication No. 2010/0304405, which is incorporated by reference herein. As shown in FIG. 7, in addition to the increased activity with PASC, CelEcc_CBM3a appears to have significant improvements of catalytic reactivity with crystalline cellulose I compared with native CelE and CelEcc. Cellulose I is the natural allomorph commonly found in biomass. For example, the catalytic reactivity of CelEcc_CBM3a with cellulose I is at least four times over that of native CelE, and the catalytic reactivity of CelEcc_CBM3a with cellulose I is at least two times over that of CelEcc. Surprisingly, the engineered construct of CelEcc_CBM3a shows even more dramatic improvement in its reaction with cellulose III, a non-natural allomorph formed during extractive AFEX pretreatment.

As shown in FIG. 7, the catalytic reactivity of CelEcc_CBM3a with cellulose III is almost five times over that of native CelE, and the catalytic reactivity of CelEcc_CBM3a with cellulose III is at least three times over that of CelEcc. Further, CelEcc_CBM3a is more reactive with cellulose III than either CelKcc or CelRcc_CBM3a (FIG. 7). As a comparison, CelRcc_CBM3a is strongly reactive with cellulose I, but weakly reactive with cellulose III, highlighting the uniqueness and the unanticipated results of the engineered construct of CelEcc_CBM3a for hydrolysis of cellulose III.

Figure 8:
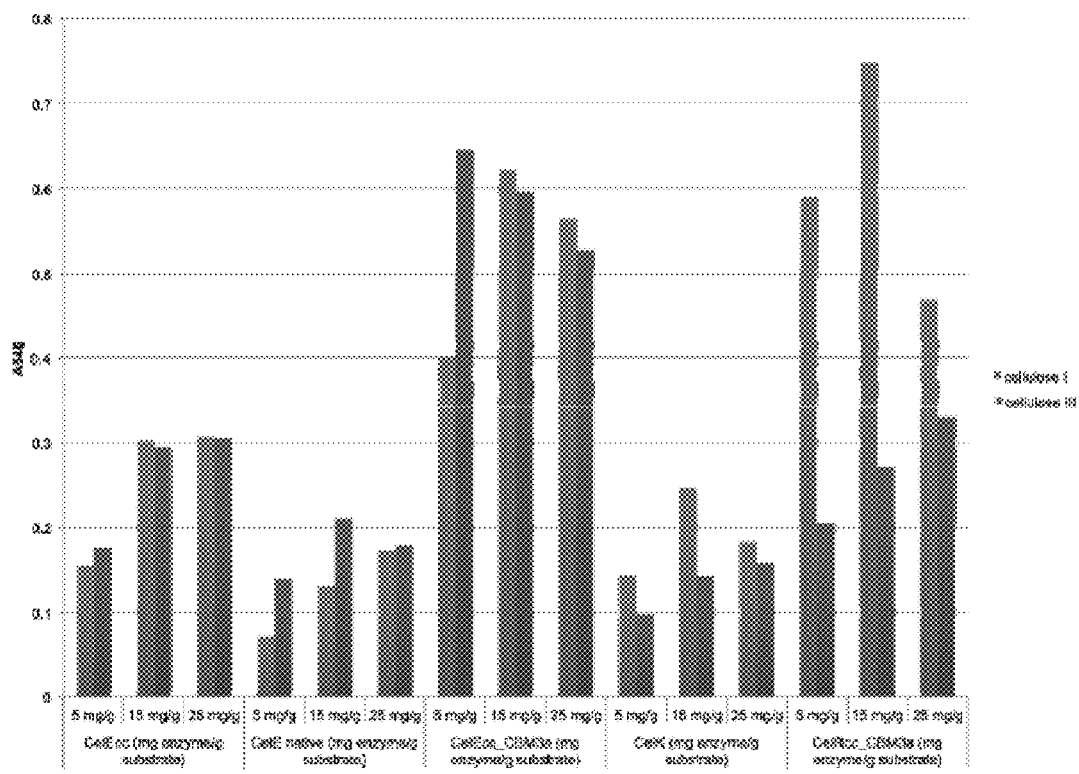
FIG. 8 is a diagram depicting a catalytic activity comparison of CelEcc, CelE native, CelEcc_CBM3a, CelK, and CelRcc_CBM3a with either cellulose I or cellulose III with different enzyme loading.
Figure 9:
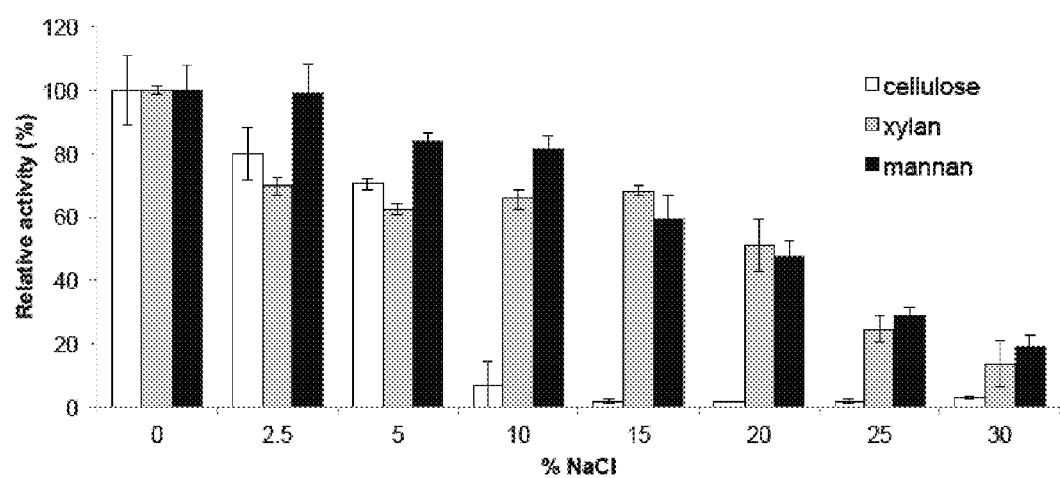
FIG. 9 is a set of diagrams demonstrating catalytic activity of CelEcc, CelE native, and CelEcc_CBM3a under various concentrations of NaCl.

One major challenge for the current biofuel industry is to minimize enzyme requirements for biomass hydrolysis, with a goal of using less than 5 mg/g (enzyme/glucan). Due to its characteristic multifunctional properties, CelEcc_CBM3a has great potential in meeting the goal of minimizing enzyme requirements for biomass hydrolysis. FIG. 8 depicts a catalytic activity comparison of CelEcc, CelE native, CelEcc_CBM3a, CelK, and CelRcc_CBM3a with either cellulose I or cellulose III with different enzyme loading. At 5 mg/g (enzyme/substrate), CelEcc_CBM3a reaches almost 80% of its maximal catalytic reactivity with cellulose I. Further, at 5 mg/g (enzyme/substrate), CelEcc_CBM3a reaches its maximal catalytic reactivity with cellulose III. By comparison, at 5 mg/g (enzyme/substrate), native CelE and CelEcc reach 50-60% of their maximal reactivity with cellulose I and cellulose III.

In one embodiment of the invention, one would apply CelEcc_CBM3a as one component enzyme of the enzyme cocktail to degrade extractive-AFEX pretreated biomass by utilizing its extraordinary catalytic reactivity with cellulose I and cellulose III. This same enzyme would also be capable of reacting with the xylan and mannan present in the biomass. Thus, due to the multifunctional property of CelEcc_CBM3a, its use would consequently minimize the number of enzymes needed in the enzyme cocktail.

In one embodiment of the invention, native CelE, CelEcc, and CelEcc_CBM3a are provided for use as enzymes or peptides which remain stable and at least partially active under harsh environments. Harsh environments may include a temperature higher than 40, 50, or even 60° C., an acidic solution with a pH value less than 6.0, 5.0 or even 4.0, and a salt solution with a concentration higher than 20%.

Native CelE, CelEcc, and CelEcc_CBM3a are found to be most catalytically reactive at pH 6.0, and they retain about 50% of the maximal catalytic reactivity at pH 4.5 and pH 7.0. Native CelE, CelEcc, and CelEcc_CBM3a are found to be most catalytically reactive at 60° C., and they retain about 50% of the maximal catalytic reactivity at 45° C. Further, native CelE, CelEcc, and CelEcc_CBM3a do not become inactive in a solution having high concentration of salt. Many of the currently utilized pretreatment processes in the biofuel industry are performed under harsh environments, including at elevated temperatures or pressures, in acidic solutions, in solutions having a high concentration of salt, etc. Thus, the pretreated biomass must be further treated before an enzyme cocktail can be introduced. This additional treatment process may require significant time and/or energy, thus increasing the cost of biofuel production. Further, current enzyme cocktails are mostly produced from mesophilic fungal sources and most of them are not stable under harsh environments.

Thus, it would be beneficial to develop an enzyme cocktail that is stable and could be added to the biomass under harsh environments. Native CelE, CelEcc, and CelEcc_CBM3a are produced by the thermophilic bacterium of *C. thermocellum*. These enzymes are stable and they remain at least partially active under the above harsh environments. Therefore, a designer enzyme cocktail including native CelE, CelEcc, or CelEcc_CBM3a could be added to the pretreated biomass under a much harsher environment than that for the current commercially available enzyme cocktails. This process would not only save time but also could result in a significant reduction in energy. The stability of native CelE, CelEcc, and CelEcc_CBM3a makes them desirable enzymes or polypeptides to add into all of the current pretreatment processes and any future pretreatments that require enzymatic activity under harsh environments.

In one embodiment of the invention, an enzyme or polypeptide composition for a mammal to increase the rate and extent of fiber digestion is disclosed. Due to their multifunctional properties and their stability under harsh environments, native CelE, CelEcc, and CelEcc_CBM3a can be used to assist in fiber digestion in a mammal. Native CelE, CelEcc, or CelEcc_CBM3a may be used individually. Native CelE, CelEcc, or CelEcc_CBM3a may also be used in a composition which includes other enzymes or polypeptides and other ingredients. The composition may be an enzyme cocktail.

A "mammal" includes all mammals, preferably humans, ruminants and monogastric animals. A ruminant includes any animal that digests plant-based food such as cattle, goats, sheep, giraffes, bison, moose, elk, yaks, water buffalo, deer, camels, alpacas, llamas, antelope, pronghorn, nilgai, kangaroos, and others. Monogastric animals that digest plant-based foods include humans, pigs, horses, rabbits, and others.

For a human, an enzyme or polypeptide composition including native CelE, CelEcc, or CelEcc_CBM3a may be used to help reduce the size of phytobezoars. A phytobezoar is a type of bezoar, or a trapped mass in the stomach, that consists of components of indigestible plant material, such as fibers, skins and seeds. While phytobezoars may be discovered incidentally on barium x-ray or endoscopic testing of the stomach, individuals with phytobezoars may develop symptoms such as nausea, vomiting, gastric outlet obstruction, perforation, abdominal pain, and even bleeding. The currently available treatments for phytobezoars include endoscopy with various assisted devices (Roth baskets, snares, or Dormia baskets), electrohydraulic lithotripsy, mechanical lithotripsy, Nd:YAG laser therapy, and even surgical gastrotomy. Native CelE, CelEcc, and CelEcc_CBM3a have multifunctional properties to hydrolyze three major components of plant cell walls, thus, a composition including Native CelE, CelEcc, and CelEcc_CBM3a may provide a cheaper and an alternative treatment solution for phytobezoars.

For a ruminant or a monogastric animal, native CelE, CelEcc, or CelEcc_CBM3a can be utilized to increase the nutritional density of animal feed. The addition of these enzymes or polypeptides to animal feed partially breaks down the recalcitrant polysaccharides of the plant cell walls, thus increasing the amount of readily available digestible sugars. This treatment allows the animal to extract more energy from the feed compared to a feed which was not treated by enzymes or polypeptides. In one embodiment, an enzyme cocktail including native CelE, CelEcc, or CelEcc_CBM3a can be utilized to partially digest the feedstock. In another embodiment, native CelE, CelEcc, or CelEcc_CBM3a could also be utilized individually to release easily digestible sugars. Further, native CelE, CelEcc, or CelEcc_CBM3a is stable and shows high catalytic activity under conditions found in the rumen (40° C. and pH 6.9). Thus, the enzymes would continue to help release sugars even after the feedstock has been ingested. Consequently, by using native CelE, CelEcc, or CelEcc_CBM3a, one would greatly simplify the complexity of the enzymes needed to partially degrade animal feed and one would drastically reduce the cost of producing multiple enzymes needed for feeding to ruminants.

Methods of the Present Invention

In one embodiment, the present invention is a method of hydrolyzing a substrate by applying native CelE, CelEcc, or CelEcc_CBM3a to the substrate. A substrate may comprise cellulosic materials, xylan, and mannan. Specifically, a substrate may include cellulose III and cellulose I. A substrate may include a material which contains one or more of cellulosic materials, such as xylan, mannan, beta-glucan, galactan, mannan, galactomannan, xylan, lichenan, and any other polysaccharide included in biomass.

Native CelE, CelEcc, or CelEcc_CBM3a is produced following the method and procedure described in U.S. Patent Publication No. 2010/0304405, which is incorporated by reference herein. The enzymes or polypeptides of native CelE, CelEcc, or CelEcc_CBM3a may be prepared as a powder or a dried or lyophilized form. Subsequently, a solution of the enzymes or polypeptides of native CelE, CelEcc, or CelEcc_CBM3a may be prepared by dissolving the powders into a suitable solvent. A suitable solvent may include water, dimethyl sulfoxide (DMSO), alcohols, acetone, and any other suitable inorganic solvents and any other suitable organic solvents. The enzymes or polypeptides of native CelE, CelEcc, or CelEcc_CBM3a may also be prepared as a solution.

Native CelE, CelEcc, or CelEcc_CBM3a may be applied individually to degrade the substrate. Native CelE, CelEcc, or CelEcc_CBM3a may also be applied in a combination with one or more of other enzymes. The enzymes may include any other celluloses, xylanases, or mannanases. In one embodiment, an enzyme cocktail including native CelE, CelEcc, or CelEcc_CBM3a may be applied to hydrolyze the substrate.

Native CelE, CelEcc, or CelEcc_CBM3a may be applied as a powder or a dried or lyophilized form. A suitable amount of native CelE, CelEcc, or CelEcc_CBM3a may be mixed with the substrate into a mixture solution. In order to effectively mix the substrate with enzymes or polypeptides, the process may include applying a mixing apparatus such as shake flasks (SFs), roller bottle reactors (RBRs), and sonicators, and conventional mixing methods such as shaking, gravitational tumbling, and hand stirring. Agricultural feeds may be mixed with the enzymes using TMR (total mixed ration) mixers, tumble drum mixers, grinder mixers, horizontal mixers, reel mixers, vertical mixers, roller mixers, and hand mixing.

The suitable amount of native CelE, CelEcc, or CelEcc_CBM3a is in the range of 1-100 mg/g (enzyme/glucan), preferably 1-10 mg/g (enzyme/glucan). The catalytic reaction takes place under suitable conditions for hydrolytic enzymes. The suitable condition may include a pH value between 4.5 and 7.0, preferably 6.0, a temperature range of 35-60° C., preferably 60° C., and a reaction time between 10-100 hours, preferably 16-24 hours, most preferably 20 hours.

In one embodiment, native CelE, CelEcc, or CelEcc_CBM3a may be applied as a solution. If one were to use a solution of native CelE, CelEcc, or CelEcc_CBM3a, an equivalent amount of native CelE, CelEcc, or CelEcc_CBM3a protein as described above will be applied.

In another embodiment, the invention is a method to treat a mammal for increasing the rate and the extent of fiber digestion using native CelE, CelEcc, or CelEcc_CBM3a. A mammal may include a human, a ruminant, and a monogastric animal. For a human, who has at least one phytobezoar in his/her stomach, the enzymes or polypeptides of native CelE, CelEcc, or CelEcc_CBM3a may be applied as a powder or a dried or lyophilized form. The enzymes or polypeptides of native CelE, CelEcc, or CelEcc_CBM3a may be taken as pills, tablets or any other solid forms. Given the sizes of the phytobezoars, the suitable amount of native CelE, CelEcc, or CelEcc_CBM3a may be in the range of 1-100 mg/g (enzyme/glucan), preferably 1-10 mg/g (enzyme/glucan). Alternatively, the enzymes or polypeptides of native CelE, CelEcc, or CelEcc_CBM3a may be applied in a solution. If one were to use a solution of native CelE, CelEcc, or CelEcc_CBM3a, an equivalent amount of native CelE, CelEcc, or CelEcc_CBM3a protein as described above will be applied.

For a ruminant, the invention is a method for increasing the digestibility of ruminant feed with enzymes or polypeptides of native CelE, CelEcc, or CelEcc_CBM3a. In one preferred embodiment, the invention is a method of applying an aqueous mixture of native CelE, CelEcc, or CelEcc_CBM3a to ruminant feed. The suitable amount of native CelE, CelEcc, or CelEcc_CBM3a to effectively digest ruminant feed is in the range of 1-100 mg/g (enzyme/glucan), preferably 1-10 mg/g (enzyme/glucan). Native CelE, CelEcc, or CelEcc_CBM3a may be initially prepared as an aqueous solution, having a concentration of 10-500 nmol/g (enzyme/glucan), preferably between 50-150 nmol/g (enzyme/glucan). In some embodiments, the concentration will be between 20-200 nmol/g (enzyme/glucan). If one were to use a solution of native CelE, CelEcc, or CelEcc_CBM3a, an equivalent amount of native CelE, CelEcc, or CelEcc_CBM3a protein as described above will be applied.

The aqueous solution of enzymes or polypeptides may be applied to the ingestible materials of ruminant feed, such as hay or other forage, immediately prior to ingestion. Preferably, the aqueous solution of enzymes or polypeptides may be sprayed using an applicator tube or a spray nozzle. To effectively mix enzymes or polypeptides with ruminant feed, the ingestible materials of ruminant feed may be mechanically turned as the spray is applied, for example using a TMR mixer, a reel or an auger. To maintain the effective catalytic activity of the enzymes or polypeptides and to increase binding of enzymes or polypeptides to fibers, the aqueous solution of enzymes or polypeptides, the ruminant feed, and the mixture may be heated to an elevated temperature such as 60° C.

The aqueous solution of enzymes or polypeptides may be applied to the ingestible materials of ruminant feed, such as hay or other forage, as part of their preparation for storage in a silo. Preferably, the aqueous solution of enzymes or polypeptides may be sprayed using an applicator tube or a spray nozzle. To effectively mix enzymes or polypeptides with ruminant feed, the ingestible materials of ruminant feed may be mechanically turned as the spray is applied, for example using a TMR mixer, reel or an auger.

EXAMPLES

Example 1

The Binding Affinity Assays of Native CelE, CelEcc and CelEcc_CBM3a

Due to weak binding ability of native CelE and CelEcc to insoluble substrates such as cellulosic materials, xylan, and mannan, it is desirable to produce an enzyme of CelEcc_CBM3a by fusing the catalytic core of the native CelE with a cellulose-specific carbohydrate-binding module (CBM3a) domain. To confirm that the engineered construct of CelEcc_CBM3a has better binding ability with insoluble substrates than native CelE and CelEcc, the experiment of binding affinity assay of native CelE, CelEcc and CelEcc_CBM3a was performed. All constructs of native CelE, CelEcc, and CelEcc_CBM3a were produced by expression in *Escherichia coli* using an auto-inducing medium containing glucose, lactose, tryptone and yeast extract at 25° C. for 24 hours. The cells were harvested by centrifuging the growth media at 3500 g for 20 minutes, as described in the previous references (Blommel, et al. 2007; Jeon, et al. 2005; Blommel and Fox, 2007). The resulting cell pellet was resuspended in 100 mM MOPS at pH 7.5, 500 mM NaCl, and 10 mM imidazole and lysed by sonication. Insoluble cellular material was removed by centrifuging the lysed samples at 75,000 g for 45 minutes. All CelE constructs were purified by immobilized metal affinity chromatography, as described in the previous references (Blommel, Becker, et al. 2007; Jeon, Aceti, et al. 2005). The enzymes were mixed with substrates, and the mixture was incubated for 1 hour at 4° C., and the mixture was then centrifuged to separate bound and unbound fraction, indicated as pellet (P) and supernatant (S), respectively.

Control experiments were carried out in the absence of substrates demonstrating that the protein precipitation did not occur due to protein aggregation or instability. The results were depicted in FIG. 5, where the substrates included crystalline cellulose (SIGMACELL-20), phosphoric acid amorphous cellulose (PASC) and mannan. As shown in FIG. 5, native CelE, which was a cellulosomal protein lacking a carbohydrate-binding module (CBM) domain, showed weak binding affinities to all three substrates of SIGMACELL-20, PASC, and mannan. Similarly, the catalytic core of native CelE (CelEcc) did not bind to the substrates of SIGMACELL-20 and mannan and CelEcc only weakly bound to PASC. In contrast, the engineered construct of CelEcc_CBM3a showed a much stronger binding affinity to all the substrates of SIGMACELL-20, PASC, and mannan. Therefore, fusion of a carbohydrate-binding module (CBM3a) onto the catalytic core of native CelE (CelEcc) increased the binding affinity of the resulting enzyme to solid substrates, thus improving the catalytic reactivity of the enzyme.

Example 2

Catalytic Activities of Native CelE, CelEcc and CelEcc_CBM3a with Cellulose I, Xylan and Mannan It was shown that CelEcc_CBM3a has a much stronger binding ability to insoluble substrates than native CelE and CelEcc. Consequently, it was expected that CelEcc_CBM3a would have a much better catalytic reactivity with the insoluble substrates than native CelE and CelEcc. The experiment regarding catalytic activities of native CelE, CelEcc and CelEcc_CBM3a with cellulose I, xylan and mannan, was thus performed. The catalytic reactions were carried out at 60° C., and the reaction time was 20 hours. The experiment was conducted with an amount of 8 mg of enzyme per gram of glucan. The products obtained in the reaction were detected by DNS assay. FIG. 6 showed that native CelE, CelEcc, and CelEcc_CBM3a had different rates and relative activities for hydrolyzing insoluble substrates. As expected, the engineered construct of CelEcc_CBM3a had a catalytic reactivity with phosphoric acid amorphous cellulose (PASC) of at least 50% higher than that of native CelE. The engineered construct of CelEcc_CBM3a had a catalytic reactivity with phosphoric acid amorphous cellulose (PASC) of at least three times over that of CelEcc. While CelEcc_CBM3a showed a comparable reactivity with xylan and mannan to that of native CelE, the presence of CBM3a increased the catalytic reactivity by about 100% compared with that of CelEcc. The results demonstrated that CelEcc_CBM3a could also hydrolyze SIGMACELL, filter paper, beta-glucan, galactan, mannan, galactomannan, xylan, and lichenan.

Example 3

Catalytic Activities of CelEcc, Native CelE, CelEcc_CBM3a, CelK, and CelRcc_CBM3a with Either Cellulose I (SIGMACELL-20) or Cellulose III Prepared from SIGMACELL-20 by Extractive AFEX Due to the specific binding ability of CBM3a, one would be interested in discovering the catalytic reactivity of the engineered construct of CelEcc_CBM3a with different insoluble substrates. Thus, an experiment regarding catalytic activities of CelEcc, native CelE, CelEcc_CBM3a, CelK, and CelRcc_CBM3a with either cellulose I or cellulose III was performed. Cellulose I was obtained directly as SIGMACELL-20, and cellulose III was prepared from SIGMACELL-20 by extractive AFEX (E-AFEX). CelKcc and CelRcc_CBM3a were produced following the same method and procedure described in U.S. Patent Publication No. 2010/0304405, which is incorporated by reference herein. The results were depicted in FIG. 7.

As shown in FIG. 7, in addition to the increased activity with PASC, CelEcc_CBM3a appeared to have significant improvements of catalytic reactivity with crystalline cellulose I, the natural allomorph commonly found in biomass. For example, the catalytic reactivity of CelEcc_CBM3a with cellulose I was found to be at least four times over that of native CelE, and the catalytic reactivity of CelEcc_CBM3a with cellulose I was found to be at least two times over that of CelEcc. Surprisingly, the engineered construct of CelEcc_CBM3a showed even more dramatic improvement in its reaction with cellulose III, a non-natural allomorph formed during extractive AFEX pretreatment. The catalytic reactivity of CelEcc_CBM3a with cellulose III was almost five times over that of native CelE, and the catalytic reactivity of CelEcc_CBM3a with cellulose III was at least three times over that of CelEcc. Further, it was found that CelEcc_CBM3a was more reactive with cellulose III than either CelKcc or CelRcc_CBM3a (FIG. 7). As a comparison, CelRcc_CBM3a was found to be strongly reactive with cellulose I, but weakly reactive with cellulose III.

Example 4

Multifunctional Catalytic Activities of CelEcc_CBM3a

Figure 10A:
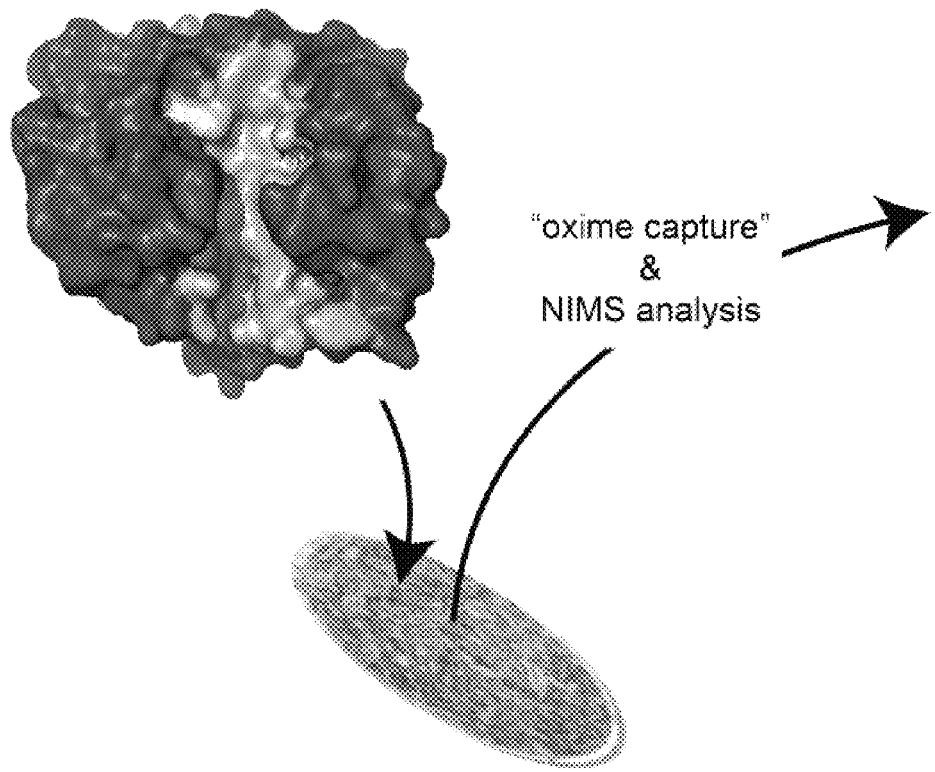
FIG. 10A is a diagram showing that CelEcc_CBM3a alone can react with biomass, e.g., AFEX-switchgrass.

FIG. 10 is a set of diagrams and graphs showing multifunctional catalytic activity of CelEcc_CBM3a. FIG. 10A is diagram showing the three-dimensional structure of CelEcc_CBM3a and indicating that CelEcc_CBM3a can be individually reacted with biomass, e.g., AFEX-switchgrass (AFEX-SG). FIG. 10B is a graph showing NIMS analysis (see Reindl, et al., 2011 and Reindl et al., 2012) of the products from the catalytic reaction of CelEcc_CBM3a (Cthe_0797; GH5) with AFEX-switchgrass. In the NIMS analysis, reducing sugars released by enzyme action from the biomass react with a mass-spectral probe containing a hydroxylamino functional group. Upon mixing and reaction, the hydroxylamino group condenses with the reducing sugar to form a stable, covalent oxime bond. After labeling, the sugars can be identified by using mass spectrometry. The individual mass spectral peaks in FIG. 10B have unique masses corresponding to the chemical structures identified. The multifunctional enzyme of CelEcc_CBM3a produces products derived from both cellulose and hemicellulose after its reaction with biomass, in this case AFEX-SG. FIG. 10C is a graph showing NIMS analysis (of the products from the catalytic reaction of BgIA (Cthe_0212; GH1) with AFEX-SG as a control experiment. The reaction of BgIA with biomass was carried out in 100 µL of 50 mM phosphate and at pH 6.0. The biomass contained 10 mg AFEX-SG. The volume of enzyme (BgIA) was 5 µL and the concentration of stock solution was 1 mg/mL. The reaction was carried out at 60° C. for up to 96 hours and samples were taken at various time points. At each of these time points, a 2 µL aliquot of the reaction mixture was transferred into a vial containing 6 µL of 100 mM glycine acetate at pH 1.2, 0.5 μL of a 50 mM aqueous solution of [U]-$^{13}$C glucose, 2 μL of $CH_3CN$, 2 μL of MeOH, 1 μL of NIMS probe [100 mM in 1:1 (v/v) $H_2O$:MeOH], and 0.1 μL of aniline. The mixture was incubated at room temperature for 16 hours. The mixture was then used in the NIMS assay.

Figure 11:
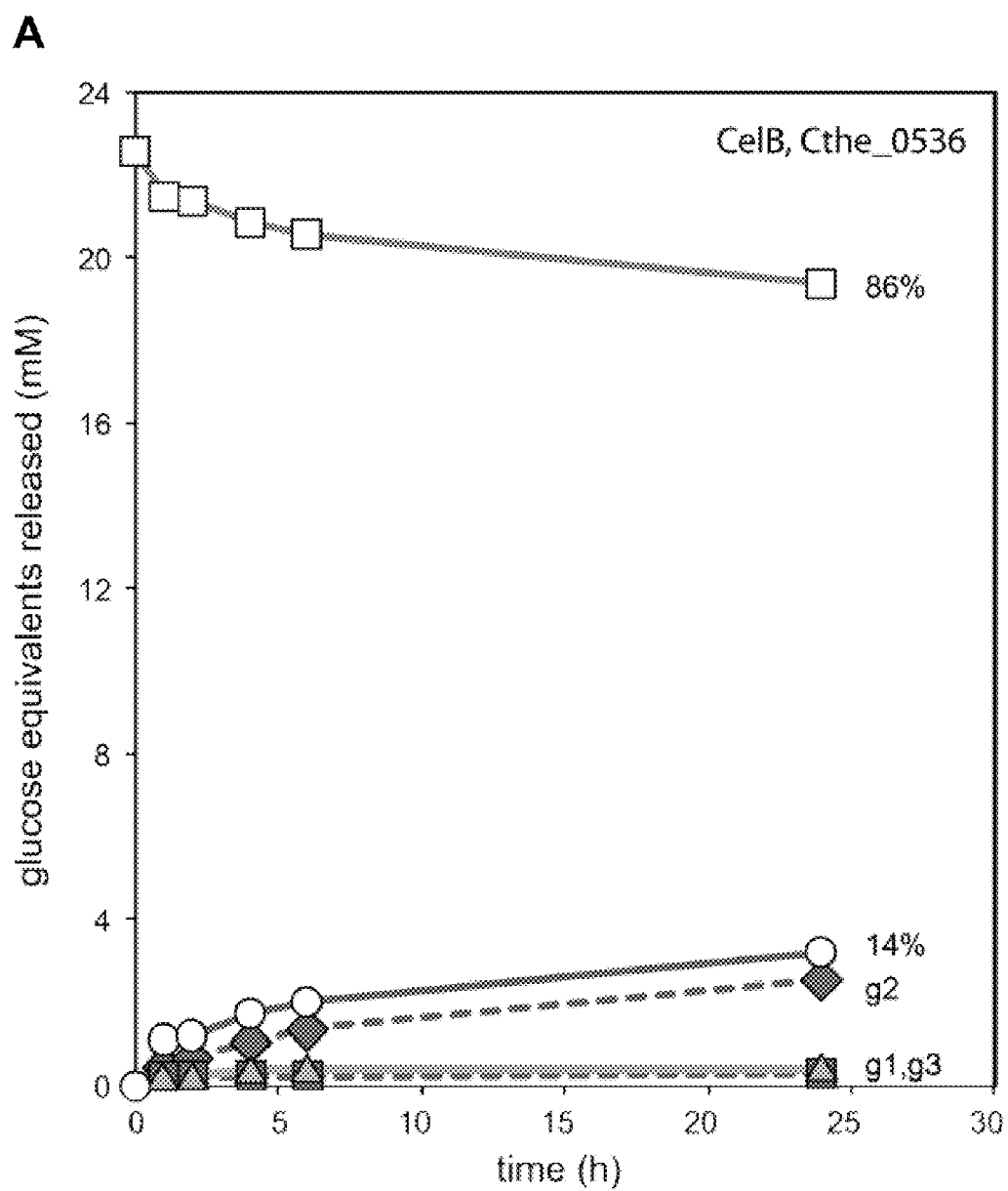
FIG. 11 is a set of graphs showing the time-dependent catalytic reactions and kinetics of enzymes with ionic-liquid treated switchgrass (IL-SG).
Figure 11:
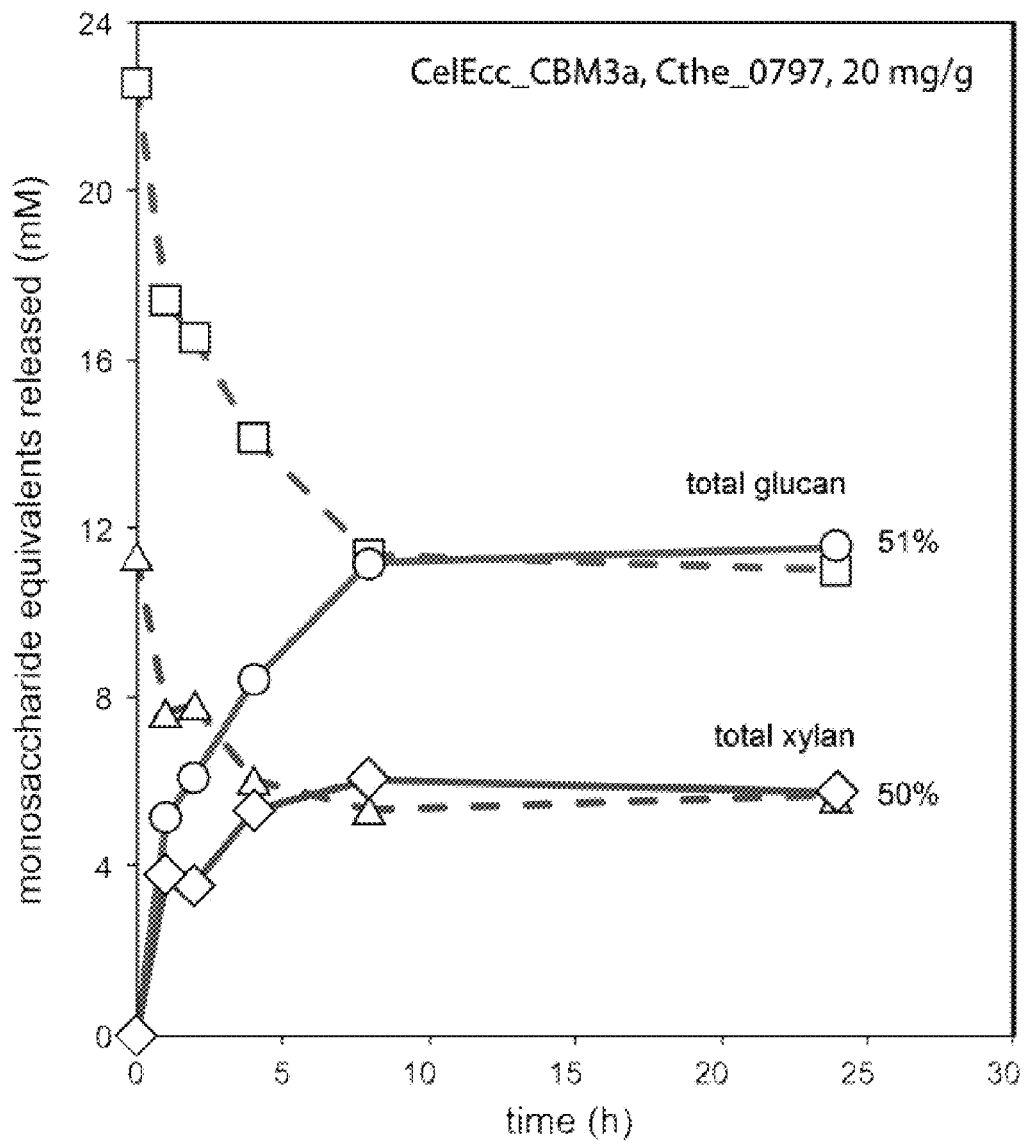

FIG. 11 is a set of graphs showing the time-dependent catalytic reactions and kinetics of enzymes with biomass, in this case ionic-liquid treated switchgrass (IL-SG). FIG. 11A is a graph showing the time-dependent catalytic reactions and kinetics of CelB (Cthe_0536) with IL-SG. The reaction of CelB with biomass was carried out in 100 μL of 50 mM phosphate at pH 6.0. The biomass contained 10 mg IL-SG. The volume of enzyme was 5 μL of CelB and the concentration of stock solution was 1 mg/mL. The reaction was carried out at 60° C. for up to 96 hours and samples were taken at various time points. At each of these time points, a 2 μL aliquot of the reaction mixture was transferred into a vial containing 6 μL of 100 mM glycine acetate at pH 1.2, 0.5 μL of a 50 mM aqueous solution of [U]-$^{13}$C glucose, 2 μL of $CH_3CN$, 2 μL of MeOH, 1 μL of NIMS probe [100 mM in 1:1 (v/v) $H_2O$:MeOH], and 0.1 μL of aniline. The mixture was incubated at room temperature for 16 hours. The mixture was then used in the NIMS assay. In the reaction of CelB, glucose (g1), cellobiose (g2), and cellotriose (g3) were observed, with cellobiose accumulating as the majority product. In total, the three hexose products accounted for only ~15% conversion of the cellulose present in IL-SG. The low yield of solubilized sugar is consistent with the known function of CelB as a non-processive endoglucanase.

FIG. 11B is a graph showing the time-dependent catalytic reactions and kinetics of CelEcc_CBM3a (Cthe_0797) with IL-SG. The reaction of CelEcc_CBM3a with biomass were carried out in 100 μL of 50 mM phosphate at pH 6.0. The biomass contained 10 mg IL-SG. The volume of enzyme was 5 μL of CelEcc_CBM3a and the concentration of stock solution was 2 mg/mL. The reaction was carried out at 60° C. for up to 96 hours and samples were taken at various time points. At each of these time points, a 2 μL aliquot of the reaction mixture was transferred into a vial containing 6 μL of 100 mM glycine acetate at pH 1.2, 0.5 μL of a 50 mM aqueous solution of [U]-$^{13}$C glucose, 2 μL of $CH_3CN$, 2 μL of MeOH, 1 μL of NIMS probe [100 mM in 1:1 (v/v) $H_2O$:MeOH], and 0.1 μL of aniline. The mixture was incubated at room temperature for 16 hours. The mixture was then used in the NIMS assay. CelEcc_CBM3a (2.2% enzyme/biomass loading w/w) simultaneously hydrolyzed cellulose and hemicellulose in the biomass to give a ~50% yield of the expected solubilized products including both hexoses and pentoses.

Figure 12:
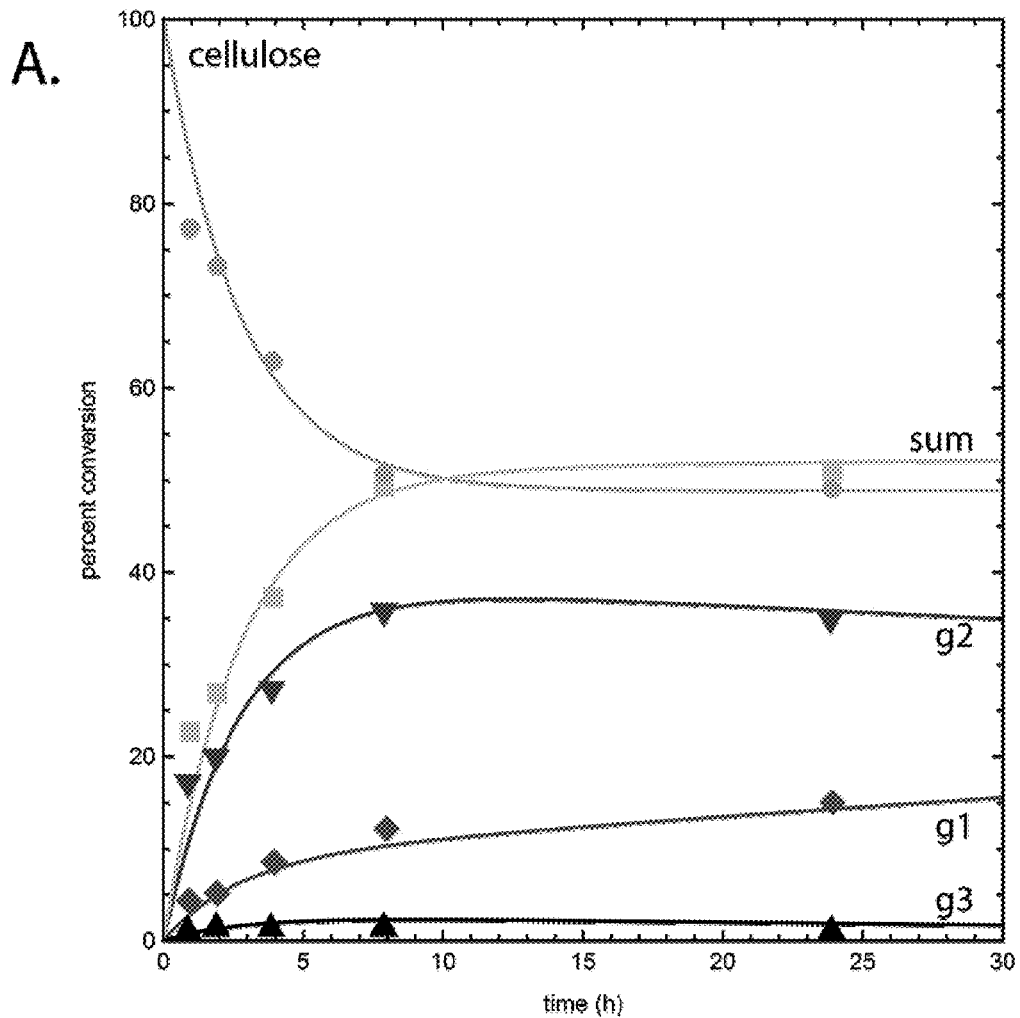
FIG. 12 is a set of graphs and diagrams showing time-dependent catalytic reactions and kinetics for the individual products derived from the reaction of CelEcc_CBM3a (Cthe_0797) with the cellulose fraction of biomass, in this case ionic liquid switchgrass (IL-SG).
Figure 12:
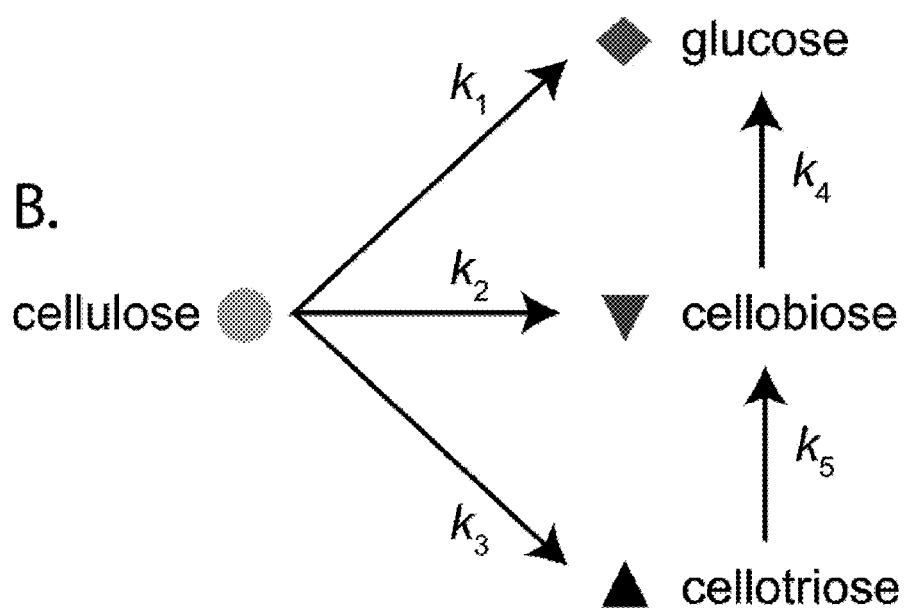
Figure 13:
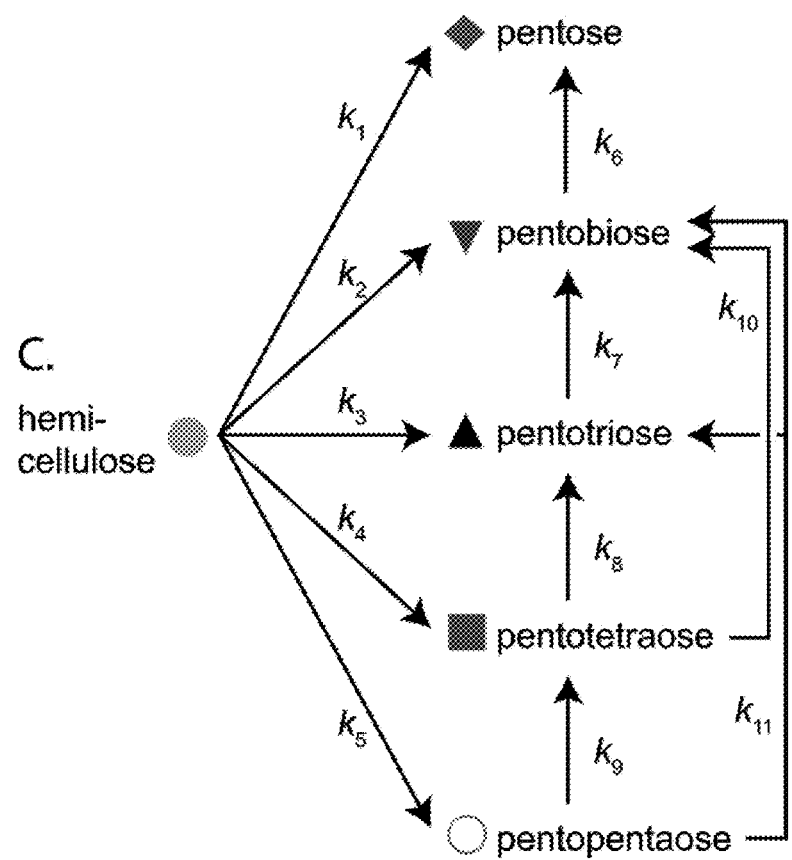
FIG. 13 is a set of graphs and diagrams showing time-dependent catalytic reactions and kinetics for the individual products derived from the reaction of CelEcc_CBM3a (Cthe_0797) with the hemicellulose fraction of biomass, in this case ionic liquid switchgrass (IL-SG).

Table 1 shows the numerical values of individual rate constants ($h^{-1}$) for the reactions with IL-SG according to the kinetic schemes shown in FIGS. 12 and 13. Rate constants were normalized to the nmol of enzyme active sites. Rate constants of $k_6$ to $k_{11}$ are not included in the kinetic scheme for cellulose reaction.

TABLE 1

Apparent rates ($h^{-1}$)$^a$ in reactions with IL-SG according to the kinetic schemes of FIG. 12 and 13.

| Rate | cellulose CelB | cellulose CelEcc_CBM3a | hemicellulose CelB | hemicellulose CelEcc_CBM3a |
|---|---|---|---|---|
| $k_1$ | 0.002 | 0.022 | 0.000 | 0.020 |
| $k_2$ | 0.027 | 0.089 | 0.000 | 0.054 |
| $k_3$ | 0.004 | 0.006 | 0.000 | 0.073 |
| $k_4$ | 0.000 | 0.002 | 0.000 | 0.059 |
| $k_5$ | 0.000 | 0.005 | 0.000 | 0.026 |
| $k_6$ | — | — | — | 0.000 |
| $k_7$ | — | — | — | 0.000 |
| $k_8$ | — | — | — | 0.000 |
| $k_9$ | — | — | — | 0.000 |
| $k_{10}$ | — | — | — | 0.000 |
| $k_{11}$ | — | — | — | 0.013 |

$^a$rates were normalized to the nmol of enzyme active sites; Rates $k_6$-$k_{11}$ are not included in the kinetic scheme for cellulose reaction.

FIG. 12 is a set of graphs and diagrams showing time-dependent catalytic reactions and kinetics of CelEcc_CBM3a (Cthe_0797) for each of the individual products from cellulose contributing to the overall reaction profile summarized in FIG. 11B. FIG. 12A shows a numerical simulation of the product evolution curves for each of the individual products detected from the reaction of CelEcc_CBM3a (Cthe_0797) with the cellulose component in IL-SG. The solid lines show the graphic results of the differential equations corresponding to the kinetic scheme shown in FIG. 12B. The differential equations for the kinetic model of FIG. 12B are provided in FIG. 12C. Table 1 shows the numerical values for the individual rate constants shown in FIG. 12B. The individual rate constants were calculated by using the differential equations shown in FIG. 12C. According to this analysis, CelEcc_CBM3a hydrolyzed 51% of the cellulose in IL-SG to a mixture of glucose (15%, relative to total cellulose in IL-SG), cellobiose (35%), and cellotriose (1%). The simulations show that CelEcc_CBM3a has a ~4.5-fold preference for releasing cellobiose from IL-SG over other products. CelEcc_CBM3a has a small propensity to release cellotriose and to hydrolyze solubilized cellotriose and cellobiose to produce other minor products. These properties correspond to reactions of purified CelEcc_CBM3a with purified cellotetraose, suggesting that the fundamental properties of the engineered enzyme are the same in reactions with biomass and the purified or artificial substrates.

FIG. 13 is a set of graphs and diagrams showing time-dependent catalytic reactions and kinetics of CelEcc_CBM3a (Cthe_0797) for each of the individual products from hemicellulose contributing to the overall reaction profile summarized in FIG. 11B. FIGS. 13A and 3B show a numerical simulations of the product evolution curves for each of the individual products detected from the reaction of CelEcc_CBM3a (Cthe_0797) with the hemicellulose component in IL-SG. The solid lines show the graphic results of the differential equations corresponding to the kinetic schemes shown in FIG. 13C. The differential equations for the kinetic model of FIG. 13C are provided in FIG. 13D. Table 1 shows the numerical values for the individual rate constants shown in FIG. 12B. The individual rate constants were calculated by using the differential equations of FIG. 13D. Since the method of NIMS cannot distinguish between the masses of various pentose isomers such as xylose, arabinose and others, generic names for pentose products were used. After 24 hours of reaction, the product formed from the reactions of CelEcc_CBM3a consists of pentose (p1, 6%, relative to total hemicellulose in IL-SG, FIG. 13A), pentobiose (p2, 16%, FIG. 13A) and pentotriose (p3, 17%, FIG. 13A), and pentotetraose (p4, 8%, FIG. 13B) and pentopentaose (p5, 3%, FIG. 13B). Table 1 shows that the apparent rates for releasing the three major products were overall similar (within ~25%).

Pentotriose accumulated at the fastest initial rate. In order to successfully model the hemicellulose product cascade, it was necessary to include slow, secondary hydrolysis of pentopentaose to pentotriose and pentobiose, and also hydrolysis of pentotetraose to 2 mol of pentobiose. Similar products were detected in the reactions of purified CelEcc_CBM3a with purified xylohexaose, indicating that CelEcc_CBM3a can react with both the insoluble hemicellulose fraction and some of the soluble pentose oligomers released from biomass.

This disclosure further incorporates the concurrently submitted sequence listing in computer readable form. The above description, attached figures and their descriptions are intended to be illustrative and not limiting of this invention, which is defined by the appended claims. Furthermore, all cited publications are incorporated by reference herein in their entirety.

REFERENCES CITED

1. Chundawat S. P., Bellesia G., Uppugundla N., Costa Sousa L., Gao D., Cheh A. M., Agarwal U. P., Bianchetti C. M., Phillips G. N., Langan P., Balan V., Gnanakaran S., and Dale B. E. *Journal of The American Chemical Society*, 2011, 133, 11163-11174.
2. Eisen N. L. and Fox B. G. U.S. Patent Publication No. 2010/0304405.
3. Blommel, P. G., K. J. Becker, P. Duvnjak and B. G. Fox. Enhanced bacterial protein expression during auto-induction obtained by alteration of lac repressor dosage and medium composition. *Biotechnol Prog.* 2007, 23, 585-598.
4. Jeon, W. B., D. J. Aceti, C. A. Bingman, F. C. Vojtik, A. C. Olson, J. M. Ellefson, J. E. McCombs, H. K. Sreenath, P. G. Blommel, K. D. Seder, B. W. Buchan, B. T. Burns, H. V. Geetha, A. C. Harms, G. Sabat, M. R. Sussman, B. G. Fox and G. N. Phillips, Jr. High-throughput purification and quality assurance of *Arabidopsis thaliana* proteins for eukaryotic structural genomics. *Journal of Structural and Functional Genomics* 2005, 6, 143-147.
5. Blommel, P. G. and B. G. Fox. A combined approach to improving large-scale production of tobacco etch virus protease. *Protein Expr. Purif.* 2007, 55, 53-68.
6. Miller, G. L. *Anal. Chem.* 1959, 31, 426-428.
7. Reindl, W., K. Deng, J. M. Gladden, G. Cheng, A. Wong, S. W. Singer, S. Singh, J. C. Lee, C. H yao, T. C. Hazen, A. K. Singh, B. A. Simmons, P. D. Adams, and T. R. Nothen. Colloid-based multiplexed screening for plant biomass-degrading glycoside hydrolase activities in microbial communities. *Energy Environ. Sci.* 2011, 4, 2884-2893.
8. Reindl, W., K. Deng, X. Cheng, A. K. Singh, B. A. Simmons, P. D. Adams, and T. R. Nothen. Nanostructure-initiator mass spectrometry (NIMS) for the analysis of enzyme activities. *Current Protocols in Chemical Biology* 2012, Jun. 1, 123-142.

We claim:

1. A multifunctional polypeptide capable of hydrolyzing a cellulosic material, xylan, and mannan, comprising
   the catalytic core (cc) of *Clostridium thermocellum* Cthe_0797 (CelE),
   a cellulose-specific carbohydrate-binding module (CBM), wherein the CBM is CBM3 of the cellulosome anchoring protein cohesion region (CipA) of *Clostridium thermocellum* (CBM3a), and
   a linker region interposed between the catalytic domain and the cellulose-specific carbohydrate binding module.

2. The polypeptide of claim 1, wherein the linker region is a 5-150 amino acid sequence.

3. The polypeptide of claim 1, wherein the linker region is a 15-40 amino acid sequence.

4. The polypeptide of claim 1, wherein the polypeptide comprises the amino acid sequence of SEQ ID NO:6.

5. A polypeptide composition for increasing the rate and the extent of fiber digestion for a mammal comprising the polypeptide of claim 1.

6. A method of hydrolyzing a substrate comprising a cellulosic material, xylan, and mannan, comprising the step of contacting a substrate comprising a cellulosic material, xylan, and mannan with an effective amount of the multifunctional polypeptide of claim 1, whereby the cellulosic material, xylan, and mannan in the substrate are at least partially hydrolyzed.

7. The method of claim 6, wherein the cellulosic material is selected from the group consisting of filter paper, crystalline cellulose allomorph I, and amorphous cellulose.

8. The method of claim 6, wherein the cellulosic material is cellulose III.

9. The method of claim 6, further comprising the step of pretreating the cellulosic material is under acidic, basic, or oxidative conditions.

10. The method of claim 8, wherein the cellulose III is a non-natural cellulose produced by extractive ammonia fiber expansion treatment of biomass.

11. The method of claim 6, wherein the substrate further comprises SIGMACELL, beta-glucan, galactan, galactomannan, or lichenan.

12. The method of claim 6, wherein the catalytic reactivity exhibited by the multifunctional polypeptide is at least 50% higher than the catalytic reactivity exhibited by native CelE.

13. The method of claim 6, wherein the catalytic reactivity exhibited by the multifunctional polypeptide is at least 1.5 times higher than the catalytic reactivity exhibited by the catalytic core (cc) of native CelE.

14. The method of claim 6, wherein the catalytic reactivity exhibited by the multifunctional polypeptide is at least 2 times higher than the catalytic reactivity exhibited by the catalytic core (cc) of native CelE.

15. The method of claim 6, wherein the method is performed at a temperature of about 60° C.

16. The method of claim 6, wherein the method is performed at a pH of about 6.0.

17. The method of claim 6, wherein the effective amount of multifunctional polypeptide is in the range of 1-100 mg/g (enzyme/glucan).

18. The method of claim 6, wherein the effective amount of multifunctional polypeptide is in the range of 1-10 mg/g (enzyme/glucan).

19. A method of increasing the rate and the extent of fiber digestion in a mammal comprising the step of administering to a mammal an effective amount of the multifunctional polypeptide of claim 1, whereby the cellulosic materials, xylan, and mannan in the fiber consumed by the mammal are at least partially hydrolyzed.

20. A method of making a multifunctional polypeptide comprises the step of linking the catalytic core (cc) of *Clostridium thermocellum* Cthe_0797 (CelE) with a cellulose-specific carbohydrate-binding module (CBM) by using a linker region, wherein the linker region is interposed between the catalytic domain and the cellulose-specific carbohydrate binding module, and wherein the CBM is CBM3 of the cellulosome anchoring protein cohesion region (CipA) of *Clostridium thermocellum* (CBM3a).

* * * * *